(12) United States Patent
Haynes et al.

(10) Patent No.: US 6,984,640 B1
(45) Date of Patent: *Jan. 10, 2006

(54) ANTIPARASITIC ARTEMISININ DERIVATIVES (ENDOPEROXIDES)

(75) Inventors: Richard K. Haynes, Kowloon (HK); William Wai-Lun Lam, Kowloon (HK); Ho-Wai Chan, New Territories (HK); Hing-Wo Tsang, New Territories (HK); Man-Ki Cheung, Laguna (HK); Gisela Greif, Remagen-Rolandswerth (DE); Gabriele Schmuck, Wuppertal (DE); Arnd Voerste, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/743,827

(22) PCT Filed: Jul. 14, 1999

(86) PCT No.: PCT/GB99/02267

§ 371 (c)(1), (2), (4) Date: Jul. 31, 2001

(87) PCT Pub. No.: WO00/04024

PCT Pub. Date: Jan. 27, 2000

(Under 37 CFR 1.47)

(30) Foreign Application Priority Data

Jul. 14, 1998 (EP) .............................. 98305596

(51) Int. Cl.
*A61K 31/54* (2006.01)
*C07D 279/10* (2006.01)
*C07D 417/00* (2006.01)
*C07D 405/00* (2006.01)

(52) U.S. Cl. ..................... 514/228.2; 544/58.2; 544/61; 544/378

(58) Field of Classification Search ............. 514/228.2, 514/450; 544/58.2, 61, 378; 549/349
See application file for complete search history.

(56) References Cited

U.S. PATENT DOCUMENTS

| 5,225,427 A | 7/1993 | Venugopalan et al. ...... 514/378 |
| 5,225,562 A | 7/1993 | McChesney et al. ........ 546/270 |
| 5,246,930 A | 9/1993 | Venugopalan et al. ... 514/232.8 |
| 6,649,647 B1 | 11/2003 | Haynes et al. .............. 514/450 |

FOREIGN PATENT DOCUMENTS

| CN | 1052673 | 3/1991 |
| CN | 1122806 | 5/1996 |
| EP | 0362730 | 4/1990 |
| EP | 0456149 | 11/1991 |
| WO | 9308195 | 4/1993 |
| WO | 9933461 | 7/1999 |

OTHER PUBLICATIONS

STN International ® CALPLUS Database, Accession No. 1999:234337; Li et al. CN 1122806 (1996), Abstract.*

Avery, M.A., Gao, F., Chong, W.K.M., Mehrotra, S., and Milhous, W.K., "Structure–Activity Relationships of the Antimalarial Agent Artemisinin. 1. Synthesis and Comparative Molecular Field Analysis of C–9 Analogs of Artemisinin and and 10–Deoxoartemisinin", J. Med. Chem. 36:4264–4275 (1993).

Meshnick, S.R., Yang, Y.-Z., Lima, V., Kuypers, F., Kamchonwongpaisan, S., and Yuthavong, Y., "Iron–Dependent Free Radical Generation from the Antimalarial Agent Artemisinin (Qinghaosu)", Microbial Agents and Chemotherapy 37(5):1108–1114 (May 1993).

Jefford, C. W., "Peroxidic Antimalarials", Adv. Drug. Res. 29:271–325 (1997).

Jung, M., and Lee, S. "A Concise Synthesis of Novel Aromatic Analgos of Artemisinin", Heterocycles 45(6): 1055–1058 (1997).

Luo, X.-D., and Shen, C.-C., "The Chemistry, Pharmacology, and Clinical Applications of Qinghaosu (Artemisinin) and its Derivatives", Med. Res. Rev. 7(1):29–57 (Jan. 1987).

Meshnick, S.R., Taylor, T.E., and Kamchonwongpaisan, S., "Artemisinin and the Antimalarial Endoperoxides: from Herbal Remedy to Targeted Chemotherapy", Microbiological Reviews 60(2): 301–315 (Jun. 1996).

Posner, G.H., "Antimalarial Peroxides in the Quinghaosu (Artemisinin) and Yingzhaosu Families", Exp. Opin. Ther. Patents 8(11): 1487–1493 (Nov. 1998).

Pu, Y. M., Torok, D. S., and Ziffer, H., "Synthesis and Antimalarial Activities of Several Fluorinated Artemisinin Derivatives", J. Med. Chem. 38(20): 4120–4124 (Jan. 1995).

(Continued)

*Primary Examiner*—Deborah C. Lambkin

(57) ABSTRACT

This invention relates to the use of certain C-10 substituted derivatives of artemisinin of general formula (I) in the treatment and/or prophylaxis of diseases caused by infection with a parasite, certain novel C-10 substituted deriviatives of artemisinin, processes for their preparation and pharmaceutical compositions containing such C-10 substituted derivatives. The compounds are particularly effective in the treatment of malaria, neosporosis and coccidiosis.

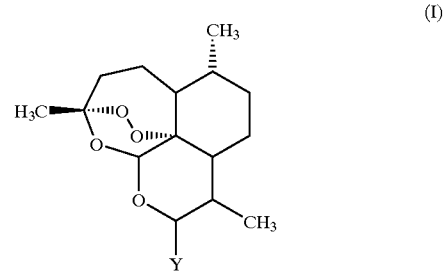

9 Claims, No Drawings

OTHER PUBLICATIONS

Tonmunphean, S., Kikpol, S., Parasuk, V., Wolschann, P., Winger, R. H. Liedl, K. R., and Rode, B. M., "Comparative Molecular Field Analysis of Artemisinin Derivatives: Ab Initio Verus Semiempirical Optimized Structures", J. Comp.–Aided Mol. Des. 12:397–409 (1998).

Yang, Y.–H., Li, Y., Shi, Y.–L., Yang, J.–D., and Wu, B.–A., "Artemisinin Derivatives with 12–Aniline Substitution: Synthesis and Antimalarial Activity", Bioorganic & Medicinal Chemistry Letters 5(16): 1791–1794 (1995).

Lin, A. J., Li, L., Klayman, D. L., George, C. F., Flippen–Anderson, J. L., "Antimalarial Activity of New Water–Soluble Dihydroartemsinin Derivatives. 3. Aromatic Amine Analogues", J. Med. Chem., 33: 2610–2614 (1990).

Meshnick, S. R., Jefford, C. W., Posner, G. H., Avery, M. A., and Peters, W., "Second–generation Antimalarial Endoperoxides", Parasitology Today, 12(2): 79–82 (1996).

Posner, G. H., Wang, D., Cumming, J. N., Oh, C. H., French, A. N., Bodley, A. L., and Shapiro, T. A., "Further Evidence Supporting the Importance of and the Restrictions on a Carbon–Centered Radical for High Antimalarial Activity of 1,2,4–Trioxanes Like Artemisinin", J. Med. Chem., 38(13): 2273–2275 (Jun. 1995).

Posner, G. H., Cumming, J. N., Ploypradith, P., and Oh, C. H., "Evidence for Fe(IV)=O in the Molecular Mechanism of Action of the Trioxane Antimalarial Artemisinin", J. Am. Chem. Soc., 117: 5885–5886 (1995).

Posner, G.H., Park, S. B., Gonzalez, L., Wang, D., Cumming, J. N., Klinedinst, D., Shapiro, T. A., and Bachi, M. D., "Evidence for the Importance of High–Valent Fe=O and of a Diketone in the Molecular Mechanism of Action of Antimalarial Trioxane Analog of Artemisinin", J. Am. Chem., 118: 3537–3538 (1996).

Pu Y. M., and Ziffer, H., "Synthesis and Antimalarial Activities of 12β–Allyldeoxoartemisinin and its Derivatives", J. Med. Chem., 38: 613–616 (1995).

* cited by examiner-

ANTIPARASITIC ARTEMISININ DERIVATIVES (ENDOPEROXIDES)

This application is a 371 of PCT/GB 99/02267 filed Jul. 14, 1999.

This invention relates to the use of certain C-10 substituted derivatives of artemisinin in the treatment and/or prophylaxis of diseases caused by infection with a parasite, certain novel C-10 substituted derivatives of artemisinin, processes for their preparation and pharmaceutical compositions containing such C-10 substituted derivatives.

Malaria is the most important human parasitic disease in the world today. Approximately 270 million people throughout the world are infected with malaria, with about 2 million dying each year. The ability of parasites to produce a complex survival mechanism by expressing variant antigens on the surface of infected erythrocytes makes it possible for the parasites to escape from the destructive action of the host immune response against these antigens. In addition, the increasing rate of malaria infection is due to the spread of chloroquine-resistant strains of *Plasmodium falciparum* and the other multi-drug resistant strains.

In the field of animal health, parasitic diseases are a major problem, especially those diseases which are functionally related to malaria. For instance, neosporosis is a term used to describe diseases caused by parasites of the species *Neospora*, especially *Neospora caninum*, in animals. *Neospora* infections are known to occur in dogs, cattle, sheep, goats and horses.

The final host for *Neospora* spp., including *Neospora caninum*, is unknown and, in addition, the complete cycle of development of the parasite is not understood. The asexual phases of reproduction, known as schizogony, and the behaviour of the unicellular tachyzoite/bradyzoite stage have been clarified, however. Tachyzoites are infectious unicellular parasite stages of about 3–7×1–5 mm in size formed after intracellular reproduction termed endodyogeny. Reproduction via tachyzoites takes place preferentially in organelles such as muscle or nerve cells. Pathological symptoms invoked after an infection are associated mainly in those tissues. Some five to six weeks after natural infection in a dog, symptoms of the disease are hypersensitivity caused by inflammation of neuronal cells and increasing tendency to hyperextension of the hind legs. Histopathological lesions are apparent in the nervous system, preferentially in the brain and spinal cord. Extensive non-suppurative inflammations, glial excrescences and perivascular infiltrations of mononuclear cells (macrophages, lymphocytes, plasma cells) dominate, and are also partly apparent in eosinophils and neutrophils. In the muscular system, macroscopically observable necroses and degenerative changes appear. Apart from the more or less strongly developed atrophy, long pale longitudinal stripes are evident.

In California and Australia, *Neospora caninum* infections appear to be the main cause for abortion in cattle. Symptoms of the disease in cattle are similar to those in the dog. Ataxia is apparent, joint reflexes are weakened and pareses at the hind legs, partly in all four legs, can be observed. The histological picture is similar to that of the dog; mainly non-suppurative meningitis and myelitis.

Data on in vivo activity of compounds suitable against neosporosis are rare because adequate in vivo test systems still have to be developed. Sulfadiazin (administered via drinking water) is effective in experimentally infected mice, only if the treatment was prophylactic, that is, the treatment was started before infection. In dogs, treatment with sulfadiazin and clindamycin is only successful if it is started early, that is, at the appearance of first clinical symptoms as a result of neuronal inflammation.

Coccidiosis, an infection of the small intestine, is relatively rarely diagnosed in humans, where it is caused by *Isospora belli*. However, humans are also the final host of at least two cyst-forming coccidial species (*Sarcocystis suihominis* and *S. bovihominis*). Consumption of raw or inadequately cooked pork or beef containing such cysts can lead to severe diarrhoea, the cause of which is probably seldom diagnosed correctly. Coccidia (phylum Apicomplexa, suborder Eimeriina) are one of the most successful groups of parasitic protozoans, having conquered virtually every class of Metazoa. The ones that are of particular importance for man are the 60–100 species which parasitise domestic animals and which in some instances can cause very severe losses, especially in poultry, although also in lambs, calves, piglets, rabbits and other animals (see Table A).

TABLE A

Causatives of intestinal coccidiosis in domestic animals

| Animal | number of Eimeria and/or Isospora species*) | most pathogenic and/or very common species (E = *Eimeria*, I = *Isospora*) |
|---|---|---|
| chicken (*Gallus callus*) | 7 | *E.tenella, E.necatrix, E.maxima, E.acervulina* |
| turkey (*Meleargidis gallopavo*) | 7 | *E.meleagrimitis, E.adenoides* |
| goose (*Anser apser*) | 6 | *E.anseris, E.truncata, E.nocens, E. kotlani* |
| duck (*Anas platyhynehus*) | 3 | *Tyzzeria perniciosa, E.anatis* |
| pigeon (*Columba livia*) | 2 | *E.columbarum, E.labbeanea* |
| rabbit (*Oryctolagus cuniculus*) | 11(12) | *E.intestinalis, E.flavescens, E.stiedai, E.magna, E.perforans* |
| sheep (*Ovis arius*) | 11(16) | *E.ovinoidalis, E.ashaza E.ovina* |
| goat (*Capra hircus*) | 12(15) | *E.ninakohlyakimovae, E.arloingi* |
| cattle (*Bos taurus*) | 12(15) | *E.zuernii, E.bovis, E.auburnensis* |
| pig (*Sus scofra*) | 7(14) | *I.suis, E.debliecki, E.scabra* |
| dog (*Canis familiaris*) | 5 | *I.canis, I. (Cystisospora) burrowsi* |
| cat (*Felis catus*) | 2 + 6 | *I.felis, I.rivolta* as final host: *Sarcocystis bovifelis, S.ovifelis, S.fusiformis, S.muris, S.cuniculi, Toxoplasma gondii* |

*)regarding to Pellerdy (1974), Eckert et al, (1995b, Levine and Ivens (1970) and Mehlhorn 1988)

Most of the pathogenic speeches are strictly host-specific. They have a complex life cycle with two asexual reproduction phases (schizogony or merogony, and sporogony) and a sexual development phase (gametogony). In view of the major importance of coccidiosis, numerous reviews are available, for instance, by Davies et al. (1963), Hammond and Long (1973). Long (1982, 1990), and Pellerdy (1974). The economically important species sometimes differ very considerably in their sensitivity to medicinal active ingredients. The sensitivity of the different developmental stages to medicinal agents also varies enormously.

As far as the use of drugs is concerned, prophylaxis is the main approach in poultry, in which symptoms do not appear until the phase of increased morbidity, and therapy is the principal strategy in mammals (McDougald 1982). Polyether antibiotics and sulfonamides, among other drug, are currently used for such treatment and prophylaxis. However, drug-resistant strains of *Eimeria* have emerged and drug-resistance is now a serious problem. New drugs are therefore urgently required. Given the multiplicity of pathogens and hosts, there is no "ideal model" for identifying and testing anticoccidial agents. For example, most of the many substances used for preventing coccidiosis in poultry are insufficiently effective or even completely infective against mammalian coccidia (Haberkorn and Mundt; 1989; Haberkorn 1996). Numerous works and sets of instructions have been published on testing of active ingredients in animals for anticoccidial efficacy, for immunisation, etc. One particularly important and comprehensive example is the survey of current methods published by Eckert et al. (1995 a).

The compound artemisinin, also known as qinghaosu (1), is a tetracyclic 1,2,4-trioxane occurring in *Artemisia annua*. Artemisinin and its derivatives dihydroartemisinin (2), artemether (3) and sodium artesunate (4) have been used for the treatment of malaria.

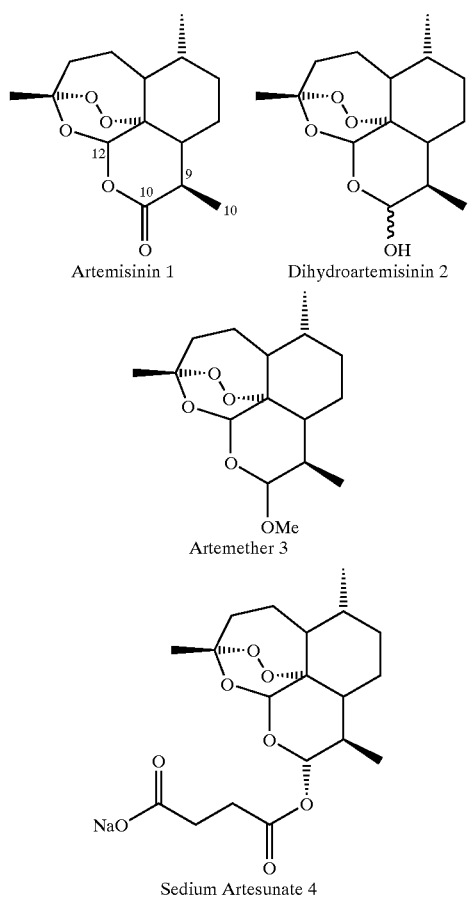

stability (Meshnick et al., *Parasitology Today* 1996, 12, 79), especially the 'first generation' ethers and esters artemether and sodium artesunate obtained from dihydroartemisinin. Extensive chemical studies carried out on artemisinin and derivatives indicate that a cause of instability is the facile opening of the trioxane moiety in artemisinin itself, or in the metabolite common to all currently, used derivatives artemether, arteether and artesunate, namely dihydroartemisinin. Ring opening will provide the free hydroperoxide, which is susceptible to reduction. Removal of this group ensures destruction of drug activity with the reduction products being transformed into desoxo metabolites. In order to render ring-opening less facile, the oxygen atom at C-10 can be either removed to provide 10-deoxydihydroartemisinin, or replaced by other groups, and this has provided the basis for the so-called 'second generation' compounds which are generally 10-deoxy artemisinin derivatives. In addition, derivatives of artemisinin have also been prepared with a variety of substituents at C-9.

Artemisinin derivatives are also known in which the oxygen atom at C-10 has been replaced by an amine group. For instance, Yang et al (Biorg. Med. Chem. Lett., 1995, 5, 1791–1794) synthesised ten new artemisinin derivatives in which the oxygen atom at C-10 was replaced by a group —NHAr where Ar represents a phenyl, 3-chlorophenyl, 4-chlorophenyl, 3-bromophenyl, 4-bromophenyl, 4-iodophenyl, 4-methylphenyl, 4-methoxyphenyl, 3-carboxylphenyl or 4-carboxylphenyl group. These compounds were tested for in viva activity against the K173 strain of *Plasmodium berohei* and found to be active.

Whilst the current artemisinin derivatives are successful, there are problems associated with stability, bioavailability and potential neurotoxicity. There is also a need for artemisinin derivatives which exhibit a broad spectrum of activity against a variety of parasites.

It has now been discovered that certain C-10 substituted derivatives of artemisinin are effective in the treatment of diseases caused by infection with a parasite. These compounds are particularly effective in the treatment of diseases caused by infection with a parasite of the genera *Plasmodium, Neospora* or *Eimeria*, especially *Plasmodium falciparum, Neospora caninum* and *Eimeria tenella* which cause malaria, neosporosis and coccidiosis respectively. According to the present invention there is therefore provided a compound of the general formula I

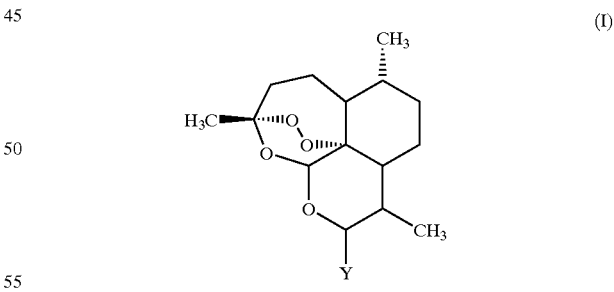

or a salt thereof,
in which
Y represents a halogen atom, an optionally substituted cycloalkyl, aryl, C-linked heteroaryl or heterocyclylalkyl group or a group —NR$^1$R$^2$; where
R$^1$ represents a hydrogen atom or an optionally substituted alkyl, alkenyl or alkynyl group;
R$^2$ represents an optionally substituted alkyl, alkenyl, alkynyl, cycloalkyl, aryl or aralkyl group; or
R$^1$ and R$^2$ together with the interjacent nitrogen atom represent an optionally substituted heterocyclic group or Different modes of action have been proposed by various groups to account for the action of artemisinin and its derivatives in treating malaria (Posner et al., *J. Am. Chem. Soc.* 1996, 118, 3537; Posner et al., *J. Am. Chem. Soc.* 1995, 127, 5885; Posner et al., *J. Med. Chem.* 1995, 38, 2273). However, irrespective of actual mode of action, all current derivatives suffer from poor oral bioavailability and poor an amino group derived from an optionally substituted amino acid ester;

for use in the treatment and/or prophylaxis of a disease caused by infection with a parasite other than an organism of the genus *Plasmodium*.

Suitable salts include acid addition salts and these way be formed by reaction of a suitable compound of formula I with a suitable acid, such as an organic acid or a mineral acid. Acid addition salts formed by reaction with a mineral acid are particularly preferred, especially salts formed by reaction with hydrochloric or hydrobromic acid. Compounds of formula I in which Y represents a group —NR$^1$R$^2$ where R$^1$ and R$^2$ are as defined above are particularly suitable for the formation of such acid addition salts.

Any alkyl, alkenyl or alkynyl group, unless otherwise specified, may be linear or branched and may contain up to 12, preferably up to 6, and especially up to 4 carbon atoms. Preferred alkyl groups are methyl, ethyl, propyl and butyl. It is preferred that any alkenyl or alkynyl group is not an alk-1-enyl or alk-1-ynyl group. In other words, there should preferably be at least one methylene group —CH$_2$— or similar sp$^3$-hybridised centre between a carbon atom forming part of the double or triple C—C bond and the nitrogen atom to which the group is attached. Preferred alkenyl and alkynyl groups include propenyl, butenyl, propynyl and butynyl groups. When an alkyl moiety forms part of another group, for example the alkyl moiety of an aralkyl group it is preferred that it contains up to 6, especially up- to 4, carbon atoms. Preferred alkyl moieties are methyl and ethyl.

An aryl group may be any aromatic hydrocarbon group and may contain from 6 to 24, preferably 6 to 18, more preferably 6 to 16, and especially 6 to 14, carbon atoms. Preferred aryl groups include phenyl, naphthyl, anthryl, phenanthryl and pyryl groups, especially a phenyl or napthyl, and particularly a phenyl, group. When an aryl moiety forms part of another group, for example the aryl moiety of an aralkyl group, it is preferred that it is a phenyl, naphthyl, anthryl, phenanthryl or pyryl, especially phenyl or naphthyl, and particularly a phenyl, moiety.

An aralkyl group may be any alkyl group substituted by an aryl group. A preferred aralkyl group contains from 7 to 30, particularly 7 to 24 and especially 7 to 18, carbon atoms, particularly preferred aralkyl groups being benzyl, naphthylmethyl, anthrylmethyl, phenanthrylmethyl and pyrylmethyl groups. A particularly preferred aralkyl group is a benzyl group.

A cycloalkyl group may be any saturated cyclic hydrocarbon group and may contain in from 3 to 12, preferably 3 to 8, and especially 3 to 6, carbon atoms. Preferred cycloalkyl groups are cyclopropyl, cyclopentyl and cyclohexyl groups.

A heteroaryl group may be any aromatic monocyclic or polycyclic ring system which contains at least one heteroatom. Preferably, a heteroaryl group is a 5–18-membered, particularly a 5- to 14-membered, and especially a 5- to 10-membered, aromatic ring system containing at least one heteroatom selected from oxygen, sulphur and nitrogen atoms. Preferred heteroaryl groups include pyridyl, pyrylium, thiopyrylium, pyrrolyl, furyl, thienyl, indolinyl, isoindolinyl, indolizinyl, imidazolyl, pyridonyl, pyronyl, pyrimidinyl, pyrazinyl, oxazolyl, thiazolyl, purinyl, quinolinyl, isoquinolinyl, quinoxalinyl, pyridazinyl, benzofuranyl, benzoxazolyl and acridinyl groups. A C-linked heteroaryl group is therefore a heteroaryl group as defined above which is linked to the tetracyclic 1,2,4-trioxane moiety of a compound of general formula I via a carbon atom in the heteroaromatic ring system.

A heterocyclic group may be any monocyclic or polycyclic ring system which contains at least one heteroatom and may be unsaturated or partially or fully saturated. The term "heterocyclic" thus includes heteroaryl groups as defined above as well as non-aromatic heterocyclic groups. Preferably, a heterocyclic group is a 3- to 18-membered, particularly a 3- to 14-membered, especially a 5- to 10-membered, ring system containing at least one heteroatom selected from oxygen, sulphur and nitrogen atoms. Preferred heterocyclic groups include the specific heteroaryl groups named above as well as pyranyl, piperidinyl, pyrrolidinyl, dioxanyl, piperazinyl, morpholinyl, thiomorpholinyl morpholinosulphonyl, tetrahydroisoquinolinyl and tetrahydrofuranyl groups.

A heterocyclylalkyl group may be any alkyl group substituted by a heterocyclic group. Preferably, the heterocyclic moiety is a 3- to 18-membered, particularly a 3- to 14-membered, and especially a 5- to 10-membered, heterocyclic group as defined above and the alkyl moiety is a $C_{1-6}$ alkyl, preferably $C_{1-4}$ alkyl, and especially methyl, group.

An amino acid may be any α-amino acid, such as glycine, alanine, valine, leucine, isoleucine, serine, threonine, cysteine, cystine, methionine, aspartic acid, glutamic acid, aspargine, glutamine, lysine, hydroxylysine, arginine, histidine, phenylalanine, tyrosine, tryptophan, proline, hydroxyproline or phenylglycine, and includes both D- and L-configurations. An amino acid ester may be any ester of such an amino acid, alkyl esters, particularly $C_{1-4}$ alkyl esters, being especially preferred.

When any of the foregoing substituents are designated as being optionally substituted, the substituent groups which are optionally present may be any one or more of those customarily employed in the development of pharmaceutical compounds and/or the modification of such compounds to influence their structure/activity, stability, bioavailability or other property. Specific examples of such substituents include, for example, halogen atoms, nitro, cyano hydroxyl, cycloalkyl, alkyl, alkenyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, alkylsulphonato, arylsulphinyl, arylsulphonyl, arylsulphonato, carbamoyl, alkylamido, aryl, aralkyl, optionally substituted aryl, heterocyclic and alkyl- or aryl-substituted heterocyclic groups. When any of the foregoing substituents represents or contains an alkyl or alkenyl substituent group, this may be linear or branched and may contain up to 12, preferably up to 6, and especially up to 4, carbon atoms. A cycloalkyl group may contain from 3 to 8, preferably from 3 to 6, carbon atoms. An aryl group or moiety may contain from 6 to 10 carbon atoms, phenyl groups being especially preferred. A heterocyclic group or moiety may be a 5- to 10-membered ring system as defined above. A halogen atom may be a fluorine, chlorine, bromine or iodine atom and any group which contains a halo moiety, such as a haloalkyl group, may thus contain any one or more of these halogen atoms.

In one aspect, it is preferred that Y represents a halogen atom, particularly a fluorine or bromine, and especially a fluorine, atom.

In another preferred aspect Y may represent a $C_{3-8}$ cycloalkyl group, a $C_{6-18}$ aryl group, a 5- to 10-membered C-linked heteroaryl group or a 5- to 10-membered heterocyclyl-$C_{1-6}$ alkyl group, each group being optionally substituted by one or more substituents selected from the croup consisting of halogen atoms, hydroxyl, $C_{1-4}$ alkyl, $C_{2-4}$ alkenyl, $C_{1-4}$ haloalkyl, $C_{1-4}$ alkoxy, amino, $C_{1-4}$ alkylamino, di(C 4 alkyl)amino, carboxyl, $C_{6-10}$ aryl, 5 to 10-membered heterocyclic and $C_{1-4}$ alkyl- or phenyl-substituted 5- to 10-membered heterocyclic groups. Preferably Y represents a $C_{6-18}$ aryl group optionally substituted by one or more substituents selected from the group consisting of halogen atoms, hydroxyl, $C_{1-4}$ alkyl, $C_{2-4}$ alkenyl, $C_{1-4}$ haloalkyl, $C_{1-4}$ alkoxy, $C_{1-4}$ haloalkoxy, amino, $C_{1-4}$ alkylamino, di($C_{1-4}$ alkyl)amino and carboxyl groups. In particular, Y may represent a phenyl, naphthyl, anthryl or phenanthryl group, each group being optionally substituted by one or more substituents selected from the group consisting of halogen atoms and hydroxyl, methyl, vinyl, $C_{1-4}$ alkoxy and carboxyl groups.

In a particularly preferred sub-group of compounds, Y represents a phenyl, fluorophenyl, chlorophenyl, bromophenyl, tri-ethylphenyl, vinylphenyl, methoxyphenyl, dimethoxyphenyl, trimethoxyphenyl, carboxylphenyl, naphthyl, hydroxynaphthyl, methoxynaphthyl, anthryl or phenanthryl group. Compounds in which Y represents a phenyl or trimethoxyphenyl group are especially preferred.

In a further preferred aspect, Y may represent a group $-NR^1R^2$ where $R^1$ represents a hydrogen atom or a $C_{1-6}$ alkyl group and $R^2$ represents a $C_{1-6}$ alkyl, $C_{3-4}$ cycloalkyl, $C_{6-10}$ aryl or $C_{7-16}$ aralkyl group, or $R^1$ and $R^2$ together with the interjacent nitrogen atom represent a 5- to 10-membered heterocyclic group or an amino group derived from a $C_{1-6}$ alkyl ester of an amino acid, each group being optionally substituted by one or more substituents selected from the group consisting of halogen atoms, $C_{1-4}$ alkyl, $C_{1-4}$ haloalkyl, $C_{1-6}$ alkoxycarbonyl, phenyl, halophenyl, $C_{3-4}$ alkylphenyl, $C_{1-4}$ haloalkylphenyl, $C_{1-4}$ alkoxyphenyl, benzyl, pyridyl and pyrimidinyl groups. In particular, Y may represent a group $-NR^1R^2$ where $R^1$ represents a hydrogen atom or a $C_{1-4}$ alkyl group and $R^2$ represents a $C_{1-4}$ alkyl, $C_{3-6}$ cycloalkyl, phenyl or benzyl group, or $R^1$ and $R^2$ together with the interjacent nitrogen atom represent a 6- to 10-membered heterocyclic group or an amino group derived from a $C_{1-4}$ alkyl ester of an amino acid, each group being optionally substituted by one or more substituents selected from the group consisting of halogen atoms, $C_{1-4}$ haloalkyl, $C_{1-4}$ alkoxycarbonyl, phenyl, halophenyl, $C_{1-4}$ alkylphenyl, $C_{1-4}$ haloalkylphenyl, $C_{1-4}$ alkoxyphenyl, benzyl, pyridyl and pyrimidinyl groups.

In a particularly preferred sub-group of these compounds, Y represents a propylamino, cyclopentylamino, cyclohexylamino, phenylamino, fluorophenylamino, chlorophenylamino, bromophenylamino, iodophenylamino, methoxycarbonylphenylamino, biphenylamino, benzylamino, fluorobenzylamino, bis(trifluoromethyl)-benzylamino, phenylethylamine, phenylmethoxycarbonyl methylamino, diethylamino, morpholinyl, thiomorpholinyl, morpholinosulphonyl, indolinyl, tetrahydroisoquinolinyl, phenylpiprerazinyl, fluorophenylpiperazinyl, chlorophenylpiperazinyl, methylphenylpiperazinyl, trifluoromethylphenylpiperazinyl, methoxyphenylpiperazinyl, benzylpiperazinyl, pyridylpiperazinyl and pyrimidinylpiperazinyl group. Compounds in which Y represents a propylamino, phenylamino, bromophenylamino, iodophenylamino, biphenylamino, benzylamino, bis(trifluoromethyl)benzylamino, phenylethylamino, phenyl-methoxycarbonylmethyl amino or morpholinyl group are especially preferred.

Preferably, the parasite is an organism of the genus *Neospora* or the genus *Eimeria*.

The present invention also provides the use of a compound of the general formula I as defined above for the manufacture of a medicament for the treatment and/or prophylaxis of a disease caused by infection as with a parasite other than an organism of the genus *Plasmodium*. Preferably, the parasite is an organism of the genus *Neospora* or the genus *Eimeria*.

Certain compounds of the general formula I are novel and the invention therefore further provides a compound of the general formula I as defined above, with the proviso that, when Y is a group $-NR^1R^2$ and $R^2$ represents a phenyl, 3-chlorophenyl, 4-chlorophenyl, 3-bromophenyl, 4-bromophenyl, 4-iodophenyl, 4-methylphenyl, 4-methoxyphenyl, 3-carboxylphenyl or 4-carboxylphenyl group, then $R^1$ is an optionally substituted alkyl group.

It should also be appreciated that the compounds of general formula I are capable of existing as different geometric and optical isomers. The present invention thus includes both the individual isomers and mixtures of such isomers.

The present invention also provides a process for the preparation of a novel compound of the general formula I as defined in the ante-preceding paragraph which comprises reacting a compound of the general formula II

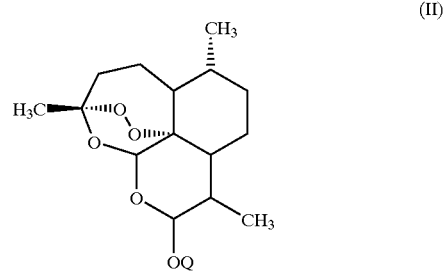

(II)

in which Q represents a hydrogen atom or trimethylsilyl group, with a suitable halogenating agent to form a compound of the general formula I in which Y represents a halogen atom; and, if desired, reacting the compound of general formula I thus formed either with a Grignard reagent of the general formula YMgX where Y is an optionally substituted cycloalkyl, aryl, C-linked heteroaryl or heterocyclylalkyl group and X is a halogen atom to form a compound of general formula I in which Y represents an optionally substituted cycloalkyl aryl, C-linked heteroaryl or heterocyclylalkyl group or with an amine of the general formula $HNR^1R^2$ where $R^1$ and $R^2$ are as defined above to form a compound of general formula I in which Y represents a group $-NR^1R^2$ where $R^1$ and $R^2$ are as defined above.

Suitable halogenating agents for forming compounds of the general formula I in which Y represents a halogen atom include diethylaminosulphur trifluoride, chlorotrimethylsilane, bromotrimethylsilane and iodotrimethylsilane. In particular, compounds of the general formula I in which Y represents a chlorine, bromine or iodine atom may be prepared by reacting a compound of the general formula II in which Q represents a trimethylsilyl croup with a suitable chlorinating, brominating or iodinating agent respectively, such as chlorotrimethlysilane, bromotrimethylsilane or iodotrimethylsilane respectively. This reaction may be conveniently carried out in the presence of a solvent. Suitable solvents include halogenated hydrocarbons, especially chlorinated hydrocarbons, such as dichloromethane. Preferably, the reaction is carried out at a temperature of $-30°$ C. to $+10°$, particularly $-5°$ C. to $+5°$ C., about $0°$ C. being especially preferred.

Compounds of the general formula I in which Y represents a fluorine atom may be conveniently prepared by reacting a compound of the general formula II in which Q represents a hydrogen atom with a suitable fluorinating agent, such as diethylaminosulphur trifluoride. This reaction may be conveniently carried out in the presence of a solvent, suitable solvents including halogenated hydrocarbons, especially chlorinated hydrocarbons, such as dichloromethane. Preferably, the reaction is carried out at −5° C. to room temperature, that is, −5 to +35° C., preferably 0 to 30° C. The reaction may also be carried out under an inert atmosphere, such as nitrogen.

Suitable Grignard reagents for forming compounds of the general formula I in which Y is an optionally substituted cycloalkyl, aryl, C-linked heteroaryl or heterocyclylalkyl group include compounds of the general formula YMgX where X represents a chlorine, bromine or iodine atom. However, it is particularly preferred that X represents a bromine atom. The reaction of a compound of the general formula I in which Y represents a halogen, preferably a bromine, atom with a Grignard reagent may be conveniently carried out in the presence of a solvent. Suitable solvents include ethers, such as diethyl ether. Preferably, the reaction is carried out under an inert atmosphere, such as nitrogen, at a temperature of −5° C. to +5° C., being especially preferred. This method produces a single pure isomer of the final product.

The reaction of an amine which a compound of the general formula I in which Y represents a halogen, preferably a bromine, atom to form a compound of the general formula I in which Y represents a group —NR$^1$R$^2$ where R$^1$ and R$^2$ are as defined above may be conveniently carried out in the presence of a solvent. Suitable solvents include halogenated hydrocarbons, especially chlorinated hydrocarbons, such as dichloromethane, and ethers, such as tetrahydrofuran. Preferably, the reaction is carried out at a temperature of −5° C. to +5° C., being especially preferred.

When a compound of the general formula I in which Y represents a bromine atom is to be further reacted with a Grignard reagent or an amine to form a compound of the general formula I in which Y represents an optionally substituted cycloalkyl, aryl, C-linked heteroaryl or heterocyclylalkyl group or a group —NR$^1$R$^2$ where R$^1$ and R$^2$ are as defined above, it is preferred that the compound of the general formula I in which Y represents a bromine atom is generated in situ by reacting a compound of the general formula II in which Q represents a trimethylsilyl croup with bromotrimethylsilane.

A compound of the general formula II in which Q represents a trimethylsilyl group may be prepared by reacting dihydroartemisinin, that is, the compound of general formula II in which Q represents a hydrogen atom, with chlorotrimethylsilane in the presence of a base, such as pyridine or triethylamine. Preferably, the reaction is carried out at room temperature, that is, 15 to 35° C., preferably 20 to 30° C.

Dihydroartemisinin, that is, the compound of general formula II in which Q represents a hydrogen atom, is a known compound and can be prepared by known processes.

Compounds of the general formula I in which Y represents an optionally substituted cycloalkyl, aryl, C-linked heteroaryl or heterocyclylalkyl group can also be prepared by reacting 9,10-anhydroartemisinin with a compound of the general formula Y—H, where Y is as defined above, in the presence of a suitable Lewis acid. This method produces a mixture of isomers in the final product.

Suitable Lewis acids include boron trifluoride dietherate and trifluoromethanesulphonic acid. The reaction may be conveniently carried out in the presence of a solvent. Suitable solvents include halogenated hydrocarbons, especially chlorinated hydrocarbons, such as dichloromethane. Preferably, the reaction is carried out under an inert atmosphere, such as nitrogen, at room temperature, that is, 15 to 35° C., preferably 20 to 30° C.

9,10-Anhydroartemisinin may be conveniently prepared by reacting dihydroartemisinin with trifluoroacetic anhydride. The reaction may be conveniently carried out in the presence of a solvent, preferably a halogenated hydrocarbon, and especially a chlorinated hydrocarbon, such as dichloromethane. It is also preferred that the reaction is carried out in the presence of a base, such as pyridine or a derivative thereof, for example, dimethylaminopyridine. Preferably, the reaction is carried out under an inert atmosphere, such as nitrogen, at a temperature of −5° C. to +5° C., preferably 0° C., with the reaction mixture being subsequently allowed to warm to room temperature, that is, 15 to 35° C., preferably 20 to 30° C.

Compounds of the general formula I in which Y represents an optionally substituted aryl or C-linked heteroaryl group can also be prepared by reacting 10-trichloroacetimidoyl-10-deoxoartemisinin with a compound of the general formula Y—H, where Y is as defined above, in the presence of a suitable Lewis acid, such as boron trifluoride diethyl etherate. It is preferred that the 10-trichloroacetimidoyl-10-deoxoartemisinin is generated in situ by reacting a compound of the general formula II in which Q represents a hydrogen atom with trichloroacetonitrile in the presence of a suitable base, such as 1,8-diazabicyclo[5.4.0]undecane. Preferably, the reaction to form 10-trichloroacetimidoyl-10-deoxoartemisinin is carried out at room temperature, that is, 15 to 35° C., preferably 20 to 30° C. The reaction may be conveniently carried out in the presence of a solvent. Suitable solvents include halogenated hydrocarbons, especially chlorinated hydrocarbons, such as dichloromethane. Preferably, the remainder of the reaction is carried out under an inert atmosphere, such as nitrogen. Preferably, the remainder of the reaction is carried out at a temperature of −60 to −20° C., particularly −55 to −30° C., and especially −40 to −50° C.

Compounds of the general formula I in which Y represents an optionally substituted aryl or C-linked heteroaryl group can also be prepared by reacting a 10-acyloxyartemisinin compound in which the acyloxy group is of formula A(C=O)—O—, where A represents an optionally substituted alkyl, cycloalkyl, aryl, aralkyl, heterocyclic or polycyclic group, with a compound of the general formula Y—H, where Y is as defined above, in the presence of a suitable Lewis acid. Suitable Lewis acids include boron trifluoride diethyl etherate, tin(IV) chloride, copper(II)-trifluoromethanesulfonate and trifluoromethanesulphonic acid. It is preferred that the Lewis acid is boron trifluoride diethyl etherate.

When A represents an optionally substituted alkyl group, unless otherwise specified, this may be linear or branched and may contain up to 12, preferably up to 6, and especially up to 4 carbon atoms. Preferred alkyl groups are methyl, ethyl, propyl and butyl.

When A represents an optionally substituted aryl group, this may be any aromatic hydrocarbon group and may contain from 6 to 24, preferably 6 to 18, more preferably 6 to 16, and especially 6 to 14, carbon atoms. Preferred aryl groups include phenyl, naphthyl, anthryl, phenanthryl and pyryl groups, especially phenyl, naphthyl and anthryl groups. When an aryl moiety forms part of another group, for example the aryl moiety of an aralkyl group, it is preferred that it is a phenyl, naphthyl, anthryl, phenanthryl or pyryl, especially a phenyl or naphthyl, and particularly a phenyl, moiety.

When A represents an optionally substituted aralkyl group, this may be any alkyl group substituted by an aryl group. A preferred aralkyl group contains from 7 to 30, particularly 7 to 24, more particularly 7 to 18, and especially 7 to 10, carbon atoms, particularly preferred aralkyl groups being benzyl, naphthylmethyl, anthrylmethyl, phenanthrylmethyl and pyrylmethyl groups, a benzyl group being especially preferred.

When A represents an optionally substituted cycloalkyl group, this may be any saturated or partially unsaturated cyclic hydrocarbon group and may contain from 3 to 12, preferably 3 to 8, and especially 3 to 6, carbon atoms. Preferred cycloalkyl groups are cyclopropyl, cyclopentyl and cyclohexyl groups.

When A represents an optionally substituted polycyclic group, this may be any saturated or partially unsaturated hydrocarbon group which contains more than one ring system. Such ring systems may be "fused", that is, adjacent rings have two adjacent carbon atoms in common, "bridged", that is, the rings are defined by at least two common carbon atoms (bridgeheads) and at least three acyclic chains (bridges) connecting the common carbon atoms, or "spiro" compounds, that is, adjacent rings are linked by a single common carbon atom. It is also envisaged that a polycyclic group may contain more than one of these types of ring system. Polycyclic groups preferably contain from 4 to 30, particularly 4 to 26, and especially 6 to 18, carbon atoms. Bicyclic, tricyclic and tetracyclic groups are particularly preferred. Preferred bicyclic groups contain from 4 to 14, especially 6 to 10, carbon atoms. Preferred tricyclic groups contain from 5 to 20, especially 6 to 14, carbon atoms with anthraquinone groups being especially preferred. Preferred tetracyclic groups contain from 6 to 26, especially 6 to 18, carbon atoms.

Optional substituents for the substituent A may be any of those previously identified as suitable in this respect.

The reaction may be conveniently carried cut in the presence of a solvent. Suitable solvents include halogenated hydrocarbons, especially chlorinated hydrocarbons, such as dichloromethane. Preferably, the reaction is carried out under an inert atmosphere, such as nitrogen. Preferably, the reaction is carried out at a temperature of −60 to −20° C., particularly −55 to −30° C., and especially −40 to −50° C.

Compounds of formula I in which Y represents a substituted aryl group where at least one of the substituents is a hydroxyl group can also be prepared by rearrangement of the corresponding C-10 ether linked artemisinin derivative so that the oxygen atom of the ether link becomes the oxygen atom of the hydroxyl group in the substituted aryl group of the desired product. Such a rearrangement can be effected by reacting the corresponding C-10 ether linked artemisinin derivative with a Lewis acid, such as a boron trifluoride dietherate. The reaction is conveniently carried out in the presence of a solvent such as dichloromethane at a temperature of −5° C. to +5° C., preferably 0° C.

Certain compounds of the general formula I may also be prepared by conversion of another compound of general formula I. For instance, 10-(4-vinylphenyl)-dihydroartemisinin may be converted to 10-(4-carboxyphenyl)dihydroartemisinin by reaction with an oxidising agent, such as potassium permanganate. Also, compounds of general formula I which contain a heterocyclic moiety having at least one sulphur atom in the ring system may be oxidised to form compounds of general formula I in which the or each sulphur atom has been converted to a sulphinyl or sulphonyl group by reaction with a suitable oxidising agent. Suitable oxidising agents include 4-methylmorpholine N-oxide (NMO), tetrapropylammonium perruthenate (TPAP) and mixtures thereof. The reaction may be conveniently carried out in the presence of a solvent, suitable solvents including halogenated hydrocarbons, especially chlorinated hydrocarbons, such as dichloromethane. Preferably, the reaction is carried out at room temperature, that is, 15 to 35° C., preferably 20 to 30° C. The reaction may also be carried out under an inert atmosphere, such as nitrogen.

The invention also provides a pharmaceutical composition which comprises a carrier and, as active ingredient, a novel compound of the general formula I as defined above.

A pharmaceutically acceptable carrier may be any material with which the active ingredient is formulated to facilitate administration. A carrier may be a solid or a liquid, including a material which is normally gaseous but which has been compressed to form a liquid, and any of the carriers normally used in formulating pharmaceutical compositions may be used. Preferably, compositions according to the invention contain 0.5 to 95% by weight of active ingredient.

The compounds of general formula I can be formulated as, for example, tablets, capsules, suppositories or solutions. These formulations can be produced by known methods using conventional solid carriers such as, for example, lactose, starch or talcum or liquid carriers such as, for example, water, fatty oils or liquid paraffins. Other carriers which may be used include materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; polypeptide/protein or polysaccharide complexes such as gelatin-acacia complexes; sugars such as mannitol, dextrose, galactose and trehalose; cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalanine.

Auxiliary components such as tablet disintegrants, solubilisers, preservatives, antioxidants, surfactants, viscosity enhancers, colouring agents, flavouring agents, pH modifiers, sweeteners or taste-masking agents may also be incorporated into the composition. Suitable colouring agents include red, black and yellow iron oxides and FD & C dyes such as FD & C blue No. 2 and FD & C red No. 40 available from Ellis & Everard. Suitable flavouring agents include mint, raspberry, liquorice, orange, lemon, grapefruit, caramel, vanilla, cherry and grape flavours and combinations of these. Suitable pH modifiers include citric acid, tartaric acid, phosphoric acid, hydrochloric acid and maleic acid. Suitable sweeteners include aspartame, acesulfame K and thaumatin. Suitable taste-masking agents include sodium bicarbonate, ion-exchange resins; cyclodextrin inclusion compounds, adsorbates or microencapsulated actives.

For treatment of and prophylaxis against coccidiosis and related parasites, for instance, in poultry, especially in chickens, ducks, geese and turkeys, 0.1 to 100 ppm, preferably 0.5 to 100 ppm of the active compound may be mixed into an appropriate, edible material, such as nutritious food. If desired, the amounts applied can be increased, especially if the active compound is well tolerated by the recipient. Accordingly, the active compound can be applied with the drinking water.

For the treatment of a single animal, for instance, for the treatment of coccidiosis in mammals or toxoplasmosis, amounts of 0.5 to 100 mg/kg body weight active compound are preferably administered daily to obtain the desired results. Nevertheless, it may be necessary from time to time to depart from the amounts mentioned above, depending on the body weight of the experimental animal, the method of application, the animal species and its individual reaction to the drug or the kind of formulation or the time or interval in which the drug is applied. In special cases, it may be sufficient to use less than the minimum amount given above, whilst in other cases the maximum dose may have to be exceeded. For a larger dose, it may be advisable to divide the dose into several smaller single doses.

The invention also includes a novel compound of the general formula I as defined above for use in the treatment and/or prophylaxis of a disease caused by infection with a parasite of the genus *Plasmodium* and use of a novel compound of the general formula I as defined above for the manufacture of a medicament for the treatment and/or prophylaxis of a disease caused by infection with a parasite of the genus *Plasmodium*. Preferred compounds in this respect include compounds of the general formula I in which Y represents a fluorine atom, Y represents a phenyl, dimethoxyphenyl or trimethoxyphenyl group or Y represents a propylamino, fluorophenylamino, biphenylamino, benzylamino, phenylethylamino, phenylmethoxycarbonyl-methylamino or diethylamino group.

The invention also provides a method for treating a disease caused by infection with a parasite other than an organism of the genus *Plasmodium* which comprises administering to a host in need of such treatment a therapeutically effective amount of a compound of the general formula I as first defined above. Preferably, the parasite is an organism of the genus *Neospora* or the genus *Eimreria*. A method for treating a disease caused by infection with a parasite of the genus *Plasmodium* is also provided which comprises administering to a host in need of such treatment a therapeutically effective amount of a novel compound of the general formula I as defined above.

The invention is further illustrated by the following examples.

EXAMPLE 1

Preparation of 10β-fluoro-10-deoxo-10-dihydroartemisinin (10β-fluoro-10-deoxodihydroartemisinin) (Formula I: Y=F)

A solution of dihydroartemisinin (1.136 g, 4 mmol) in dichloromethane (24 ml) was cooled to 0° C. under nitrogen and diethylaminosulphur trifluoride (DAST) (0.6 ml, 4.8 mmol) was added. The reaction mixture was allowed to warm up to room temperature and then stirred under nitrogen for 24 hours. The yellow solution was cooled again to 0° C., Na 2 CO₃ solution (5% 20 ml) was added and the mixture was stirred for 2 hours at room temperature. After this the two phases were separated and the organic layer was washed with 1 molar HCl, 5% NaHCO₃ and water and dried over MgSO₄. Immediately after evaporating the solvent, the residue was purified twice by flash colum chromatography (10% ethyl acetate/hexane), followed by recrystallisation from hexane (289 mg, 50.5%); $^1$H NMR(300 MHz, CDCl₃): δppm 0.97 (d, $J_{6-Me,6}$=6.1 Hz, 3H, 6-CH 3), 1.00 (d, $J_{9-Me,9}$=7.4 Hz, 3H, 9-CH₃), 1.13–1.47 (m, 3H), 1.44 (s, 3H, 3-CH₃), 1.47–1.72 (m, 4H), 1.82–1.96 (m, 2H), 2.05 (ddd, J=14.6 Hz, J=4.9 Hz, J=3.0 Hz, 1H), 2.39 (td, J=13.5 Hz, J=4.0 Hz, 1H), 2.64 (dm, $J_{9,F}$=36.1 Hz, 1H, H-9), 5.60 (dd, $J_{10,F}$=54.4 Hz, $J_{10,9}$=2.4 Hz, 1H, H-10), 5.56 (d, J=1.83 Hz, 1H, H-12); $^{19}$F NMR(282 MHz, CDCl₃): δ(ppm)=−136.43 (dd, $J_{F,10}$=54.1 Hz, $J_{F,9}$=36.0 Hz); MS (CI,NH₃) m/z (%)= 304 [M⁺+NH₄⁺] (18), 286 [M⁺], 284 [304-HF] (100), 267 (64), 256 (28), 239 (16), 221 (12), 163 (B), 52 (28).

EXAMPLE 2

Preparation of 10β-phenyl-10-deoxo-10-dihydroartemisinin (10β-(phenyl) dihydroartemisinin) (Formula I: Y=phenyl)

(a) Preparation of 10-(trimethylsiloxy) dihydroartemisinin (Formula II: O=—Si(CH₃)₃)

Method 1

To a solution of dihydroartemisinin (1.51 g, 5.32 mmol) in pyridine (20 ml) at 0° C. under nitrogen was added dropwise chlorotrimethylsilane (5.20 ml, mmol). The mixture was stirred at room temperature for a further 1 hour and poured into ice-water mixture. The solution was extracted with diethyl ether (3×15 ml), dried (MgSO₄) and concentrated in vacuo. The residue was purified by flash chromatography (SiO₂; 5% ethyl acetate/hexanes) to give 10-(trimethylsiloxy)dihydroartemisinin as a white solid (1.47 g, 78%) $δ_K$; 5.49 (1H, s, H-12), 5.19 (1H, d, J=3.05 Hz, H-10), 2.52–2.62 (1H, m, H-9), 2.39 (1H, ddd, J=17.5, 13.4, 4.01 Hz), 2.04 (1H, ddd, J=14.5, 4.84, 3.05 Hz), 1.20–1.97 (9H, m), 1.45 (3H, S, H-14), 0.97 (3H, d, j=6.24 Hz, H-16), 0.87 (3H, d, J=7.29 Hz, H-15), 0.17 (9H, s, (C$\underline{H}$₃)₃Si).

Method 2

Preparation of 10α-(trimethylsiloxy) dihydroartemisinin (Formula II: O=—Si (CH₃)₃)

To a solution of dihydroartemisinin (1.51 g, 5.32 mmol) in dichloromethane (40 ml) at 0° C. under nitrogen was added dropwise triethylamine (0.94 ml, 6.65 mmol) and chlorotrimethylsilane (0.84 ml, 6.65 mmol). The mixture was stirred at room temperature for a further 1 hour and poured into ice-water mixture. The aqueous solution was extracted with dichloromethane (2×20 ml). The combined organic layers were dried (MgSO₄) and concentrated in vacuo. The residue was purified by flash chromatography (SiO₂; 5% ethyl acetate/hexanes) to give 10α-(trimethylsiloxy)dihydro-artemisinin as a white solid (1.48 g, 78%). $δ_H$5.32 (1H, s, H-12), 4.76 (1H, d, J=9.00 Hz, H-10), 2.25–2.45 (2H, m, H-8, H-9), 2.01 (1H, m, H-4), 1.89 (1H, m, H-5), 1.18–1.79 (8H, m, H-2a, H-2b, H-3a, H-3b, H-6a, H-6b, H-7a, H-7b), 1.31 (3H, s, 1-CH₃) 0.95 (3H, d, J=5.86 Hz, 9-CH₃), 0.86 (3H, d, J=7.14 Hz, 5-CH 3), 0.20 (9H, s, Me₃Si) ppm.

(b) Preparation of 10-bromo-10-deoxo-10-dihydroartemisinin (10-bromoartemisinin) (Formula I: Y=Br)

A solution of 10α-(trimethylsiloxy)dihydroartemisinin (372 mg, 1.04 mmol) prepared as described in (a) Method 2 above in dichloromethane (5 ml) at 0° C. was treated dropwise with bromotrimethylsilane (140 μl, 1.06 mmol). The mixture was stirred at 0° C. for a further 30 minutes to produce 10-bromoartemisinin in situ.

(c) Preparation of 10β-phenyl-10-deoxo-10-dihydroartemisinin(10β-(Phenyl)dihydroartemisinin) (Formula I: Y=Phenyl)

The solution prepared in (b) above was concentrated in vacuo. The residue was dissolved in diethyl ether (5 ml). To this solution was added phenylmagnesium bromide (1.40 ml, 2.38 mmol, 1.7M) at 0° C. under nitrogen. The mixture was then stirred at 0° C. and then allowed to reach room temperature overnight. The solution was then quenched with saturated ammonium chloride solution, dried (MgSO$_4$) and concentrated in vacuo. The residue was purified by flash chromatography (SiO$_2$; 8% ethyl acetate/hexanes to give 10β-phenyl-10-deoxo-10-dihydroartemisinin (10β-(phenyl)dihydroartemisinin) (159 mg, 45%) as a white solid. Recrystallisation from ether/hexane mixture gave a colourless rectangular crystal. M.p. 122° C.; [α]$_D^{20}$ –36.0° (c 0.47/CHCl$_3$); ν$_{max}$ (film)

2938, 2874, 1494, 1452, 1376, 1208, 1112, 1076, 1058, 1038, 1010, 954, 944, 904, 882, 852, 820, 740, 700; δ$_H$, 7.19–7.34 (5H, m, Ar—H), 5.75 (1H, d, J=6.70 Hz, H-10), 5.60 (1H, s, H-12), 2.71–2.84 (1H, m, H-9), 2.31–2.42 (1H, m), 1.65–2.12 (5H, m), 1.28–1.60 (5H, m), 1.41 (3H, s, H-14), 1.01 (1H, d, J=5.77 Hz, H-16), 0.54 (1H, d, J=7.68 Hz, H-15); δ$_c$ 141.03, 127.67, 126.24, 126.09, 102.22, 90.82, 81.10, 72.99, 51.46, 43.45, 37.46, 36.64, 34.16, 32.08, 25.68, 24.88, 24.71, 19.85, 13.62; m/z (CI, CH$_4$) 345 (M$^+$+1, 14%), 327 (14), 299 (100); Anal. Calc. for C$_{22}$H$_{28}$O$_4$: C, 73.26; H, 8.14; Found: C, 73.58; H, 8.32.

nOe-difference experiment: irradiation of the doublet signal of H-10 at δ5.75 gave 10% enhancement in the multiplet signal of H-9 at δ2.75; this showed that the stereochemistry of H-10 and H-9 are syn to each other.

EXAMPLE 3

Preparation of 10α-(4'-fluorobenzylamino)-10-deoxo-10-dihydroartemisinin (10α-(4'-fluorobenzylamino)dihydroartemisinin) (Formula I: Y=—NR$^1$R$^2$; R$^1$=H; R$^2$=4-F benzyl)

(a) Preparation of 10α-(trimethylsiloxy)dihydroartemisinin (Formula II: O=—Si(CH$_3$)$_3$)

To a solution of dihydroartemisinin (1.51 g, 5.32 mmol) in dichloromethane (40 ml) at 0° C. under nitrogen was added dropwise triethylamine (0.94 ml, 6.65 mmol) and chlorotrimethylsilane (0.84 ml, 6.65 mmol). The mixture was stirred at room temperature for a further 1 hour and poured into ice-water mixture. The aqueous solution was extracted with dichloromethane (2×20 ml). The combined organic layers were dried (MgSO$_4$) and concentrated in vacuo. The residue was purified by flash chromatography (SiO$_2$; 5% ethyl acetate/hexanes) to give 10α-(trimethylsiloxy)dihydroartemisinin as a white solid (1.48 g, 78%). δ$_H$ 5.32 (1H, s, H-12), 4.76 (1H, d, J 9.00 Hz, H-10), 2.25–2.45 (2H, m, H-8, H-9), 2.01 (1H, m, H-4), 1.89 (1H, m, H-5), 1.18–1.79 (8H, m, H-2a, H-2b, H-3a, H-3b, H-6a, H-6b, H-7a, H-7b), 1.31 (3H, s, 1-CH$_3$) 0.95 (3H, d, J 5.88 Hz, 9-CH 3), 0.86 (3H, d, J=7.14 Hz, 5-CH$_3$), 0.20 (9H, s, Me$_3$Si) ppm.

(b) Preparation of 10α-(4'-fluorobenzylamino)-10-deoxo-10-dihydroartemisinin (10α-(4'-fluorobenzylamino)dihydroartemisinin) (Formula I: Y=—NR$^1$R$^2$; R$^1$=H; R$^2$=4-F-benzyl)

A solution of 10α-(trimethylsiloxy)dihydroartemisinin (214 mg, 0.600 mmol) prepared as described in (a) above in dichloromethane (5 ml) at 0° C. was treated dropwise with bromotrimethylsilane (80 μl, 0.600 mmol). The mixture was stirred at 0° C. a further 30 minutes after which it was then transferred by cannula into a solution of 4-fluorobenzylamine (140 μl 1.20 mmol) in tetrahydrofuran (5 ml) at 0° C. The mixture was stirred at 0° C. and then allowed to reach room temperature overnight. The suspension was washed with saturated NaHCO$_3$ solution, dried (MgSO$_4$) and concentrated in vacuo. The residue was purified by flash chromatography (SiO$_2$; 15% ethyl acetate/hexanes) to give 10α-(4'-fluorobenzylamino)-10-deoxo-10-dihydroartemisinin (10α-(4'-fluorobenzylamino)-dihydroartemisinin) (76.9 mg, 33%) and 9,10-anhydro-10-deoxoartemisinin (9,10-anhydro-dehydroartemisinin) (84.7 mg, 53%), both as white solids. M.p. 45.2–46.3° C.; [α]$_D^{20}$ –18.2 (c 0.055 CHCl$_3$); δ$_H$ 7.32–7.37 (2H, m, Ar—H), 6.95–7.02 (2H, m, Ar—H), 5.29 (1H, s, H-12), 4.10 (1H, d, J=13.8 Hz, H-1'), 4.08 (1H, d, J=9.76 Hz, H-10), 3.91 (1H, d, J=13.8 Hz, H-1'), 2.33–2.42 (2H, m), 1.85–2.07 (3H, m), 1.65–1.77 (2H, m), 1.03–1.75 (5H, m), 1.46 (3H, s, H-14), 0.96 (3H, d, J=6.02 Hz, H-16), 0.93 (3H, d, J=7.19 Hz, H15); δ$_c$ 136.42 (d, J=3.10 Hz), 129.30 (d, J=7.97 Hz), 114.75 (d, J=21.1 Hz), 103.90, 91.35, 85.47, 80.*60, 51.66, 47.50, 45.82, 37.23, 36.26, 34.03, 32.72, 26.03, 24.61, 21.70, 20.15, 14.06; δ$_F$ –118; m/z (CI, CH$_4$) 392 (M$^+$+1, 90%), 374 (54) 346 (100), 328 (20), 267 (16), 209 (16), 165 (26), 109 (18). Anal. Calc. for C$_{22}$H$_{30}$NO$_4$F: C, 67.50; H, 7.72; N, 3.58; Found: C, 67.51; H, 7.77; N, 3.49.

EXAMPLE 4

Preparation of 10-(2',4'-dimethoxyphenyl)-10-deoxo-10-dihydroartemisinin (10-(2',4'-dimethoxyphenyl)dihydroartemisinin (Formula I Y=2,4-dimethoxyphenyl)

(a) Preparation of 9,10-anhydro-10-deoxoartemisinin (9,10-anhydroartemisinin)

To absolution of dihydroartemisinin (500 mg, 1.86 mmol) in dichloromethane (28 ml) at 0° C. under nitrogen was added 4-(N,N-dimethylamino)pyridine (37 mg) and trifluoroacetic anhydride (0.79 ml, 5.58 mmol). The mixture was allowed to warm to room temperature and stirred overnight. The solution was then concentrated in vacuo. The residue was purified by flash chromatography (SiO$_2$; ether:hexane from 0.5:9.5 to 1.5:8.5) to give 9,10-anhydro-10-deoxoartemisinin (9,10-anhydroartemisinin) (180 mg, 25%) as a white solid. M.p. 100° C.; [α]$_D^{20.5}$ +155.74° (c. 0.0101 in CHCl$_3$); ν$_{max}$ (film): 2948, 2922, 2862, 2850, 1684, 1432, 1372, 1334, 1198, 1178, 1158, 1142, 1114, 1078, 1028, 1016, 992, 954, 944, 904, 880, 828, 812; δ$_H$, 6.18 (1H, s, H-10), 5.54 (1H, s, H-12), 2.40 (1H, ddd, J=17.1, 13.2, 4.14 Hz, H-9), 2.00–2.05 (2H, m), 1.88–1.95 (1H, m), 1.07–1.73 (8H, m), 1.58 (3H, d, J=1.37 Hz, H-16), 1.42 (3H, s, H-14), 0.98 (3H, d, J=5.98 Hz, H-1 S); m/z (EI) 380 (M$^+$); Anal. Calc. for C$_{15}$H$_{22}$O$_4$: C, 67.67; H, 8.27; Found: C, 67.63; H, 8.51.

(b) Preparation of 10-(2',4'-dimethoxyphenyl-10-deoxo-10-dihydroartemisinin (10-(2',4'-dimethoxyphenyl)-dihydroartemisinin) (Formula I: Y=2,4-dimethoxyphenyl)

To a solution of 9,10-anhydro-10-deoxoartemisinin (9,10-anhydroartemisinin) (191 mg, 0.71 mmol) prepared as described in (a) above and 1,3-dimethoxybenzene (130 μl, 1.00 mmol) in dichloromethane (10 ml) at room temperature under nitrogen was added boron trifluoride diethyl etherate (2 drops). The solution was stirred for a further 1 hour, and then quenched with 20% hydrochloric acid solution 5 ml). The mixture was extracted with diethyl ether (3×20 ml), and the ether extracts were dried (MgSO$_4$) and concentrated in vacuo. The residue was purified by flash chromatography (SiO$_2$; 15% ethyl acetate/hexanes) to give 10-(2',4'-dimethoxyphenyl)-10-deoxo-10-dihydroartemisinin (10-(2', 4'-dimethoxyphenyl)dihydroartemisinin) (89.5, 44%) as a white solid. $\delta_H$ 7.56 (1H, brd, J=8.4 Hz, Ar—H), 6.40–6.58 (2H, m, Ar—H), 5.43 (1H, s, H12), 5.42 (1H, s, H-12'), 5.16 (1H, d, J=10, =10.8 Hz, H-10), 4.96 (1H, d, J=10.3 Hz, H-10'). 3.82, 3.78 (OMe), 2.37–2.48 (2H, m), 1.05–2.07 (10H, m), 1.63 (3H, s, H-14), 1.34 (3H, s, H-14'), 1.00 (3H, d, J=6.22 Hz, H-16'), 0.90–0.93 (3H, m, H-15 & H-16); 0.59 (3H, d, J=7.22 Hz, H-15'); m/z (CI, NH$_3$) 422 (M+NH$_4^+$, 26%), 406 (84), 405 (M$^+$+1, 54), 389 (80), 359 (100), 330 (30), 317 (40), 300 (14). Anal. Calc. for $C_{23}H_{32}O_6$: C, 68.29; H, 7.97%; Found: C, 68.34; H, 8.09.

EXAMPLE 5

Preparation of 10α-(2'-hydroxy-1'-naphthyl)dihydro artemisinin (Formula I: Y=2-OH naphthyl)

(a) Preparation of 10β-(2'naphthoxy)-dihydroartemisinin

To a solution of dihydroartemisinin (568 mg, 2.00 mmol) and 2-naphthol (288 mg, 2.00 mmol) in tetrahydrofuran (10 ml) was added triphenylphosphine (524 mg, 4.00 mmol) and diethyl azodicarboxylate (330 µl, 2.00 mmol) at ° C. under nitrogen. The mixture was stirred at room temperature overnight. The yellow solution was then concentrated in vacuo and the residue purified by flash chromotography (SiO$_2$; 5% ethyl acetate/hexanes) to give 10β-(2'-naphthyloxy)dihydroartemisinin (185 mg, 23%) as a white solid.

(b) Preparation of 10α-(2'-hydroxy-1'-naphthyl)-dihydroartemisinin

To a solution of 10β-(2'-naphthoxy)dihydroartemisinin (232 mg, 0.564 mmol) prepared as described in (a) above in dichloromethane (10 ml) was added boron trifluoride dietherate (220 µl) at 0° C. The mixture was allowed to warm to room temperature and stirred for a further 30 minutes. The solution was washed with 10% sodium hydrogen carbonate solution (2×50 ml), dried (MgSO$_4$) and concentrated in vacuo. The residue was then purified by flash chromatography (SiO$_2$; 10% ethyl acetate/hexanes) to give 10α-(2'-hydroxy-1'-naphthyl)-dihydroartemisinin as a white solid (72.7 mg). $\delta_H$ 8.91 (1H, s, OH), 7.28–7.91 (6H, m, Ar—H), 5.57 (1H, s, H-12), 3.11–3.19 (1H, m), 1.28–2.55 (11H, m), 1.51 (3H, s, H-14), 1.04 (3H, d, J=5.96 Hz, H-16), 0.63 (3H, d, J=7.23 Hz, H-16).

EXAMPLE 6

Preparation of 10α-(4'-thiomorpholino-1'-yl)-10-deoxo-10-dihydroartemisinin (10α-(thiomorpholino) dihydro artemisinin) (Formula I: Y= thiomorpholino)

Reaction of bromide prepared from 10α-(trimethylsiloxy) dihydroartemisnin (356 mg, 1.00 mmol) as described in Example 3 (b) above with thiomorpholine (300 µl, 3.00 mmol) afforded 10α-(thiomorpholino)-dihydroartemisinin (243 mg, 66%) as a white solid after flash chromatography (8% ethyl acetate/hexanes). M.p. 147.0–147.6° C.; $[\alpha]_D^{20}$ +17° (c 0.021/CHCl$_3$); $v_{max}$ (film) 2924, 2872, 1454, 1418, 1376, 1326, 1278, 1226, 1198, 1184, 1154, 1130, 1100, 1056, 1038, 1018, 988, 940, 926, 880, 850, 828, 756; $\delta_H$ 5.23 (1H, s, H-12), 3.93 (1H, d, J=10.21 Hz, H-10), 3.20–3.28 (2H, m), 2.85–2.93 (2H, m), 2.53–2.68 (5H, m), 2.25–2.36 (1H, m), 1.93–2.01 (1H, m), 1.78–1.86 (1H, m), 1.63–1.70 (2H, m), 1.14–1.52 (5H, m), 1.36 (3H, s, H-14), 0.90–1.04 (1H, m), 0.91 (3H, d, J=6.14 Hz, H-16), 0.76 (3H, d, J=7.18 Hz, H-15); $\delta_c$: 103.70, 92.28, 91.42, 80.11, 51.54, 50.39, 45.66, 37.19, 36.14, 34.12, 28.15, 25.84, 24.59, 21.44, 20.15, 13.41; m/z (CI, NH 3) 370 (M$^+$+1, 100), 324 (70), 310 (10); Anal. Cal. for $C_{19}H_{31}NO_4S$: C, 61.76; H, 8.46; N, 3.79%; found C, 62.04; H, 8.39; N, 3.65.

EXAMPLE 7

Preparation of 10α-(4'-(S,S-dioxothiomorpholin-1'-yl)-10-deoxo-10-dihydroartemisinin (10α-(4'-morpholinosulphonyl)dihydroartemisinin) (Formula I: Y=4-(S,S-dioxothiomorpholin-1'-yl) (4-morpholinosulphonyl)

To a solution of 10α-(4'-thiomorpholino)-10-deoxo-10-dihydroartemisinin (10α-(thiomorpholin)-dihydroartemisinin) (388 ms, 1.05 mmol) prepared as described in Example 6 above in dichloromethane (10 ml) at room temperature under nitrogen was added NMO (369 mg, 3.15 mmol), powdered molecular sieve (525 mg, 4 Å), and TPAP (18.5 mg, cat.). The mixture was stirred at room temperature overnight after which it was filtered through a pad of SiO$_2$ and the residue was washed with ethyl acetate (3×15 ml). The filtrate was concentrated in vacuo. The residue was then purified by flash chromatography (SiO$_2$; 35% ethyl acetate/hexanes) to give 10α-(4'-(S,S-dioxothiomorpholin-1'-yl)-10-deoxo-10-dihydroartemisinin (10α-(4'-morpholinosulphonyl)-dihydroartemisinin) as a white solid (421 mg, 100%). M.p. 152.3–152.7° C.; $[\alpha]_D^{20}$ +13° (c 0.035/CHCl$_3$); $v_{max}$ (film) 2928, 2872, 1454, 137.8, 1308, 1270, 1228, 1198, 1124, 1040, 1018, 976, 940, 878, 846, 826, 752, 704, 666; $\delta_H$, 5.27 (1H, s, H-12), 4.21 (1H, d, J=10.30 Hz, H-10), 3.18–3.46, (8H, m), 2.54–2.62 (1H, m), 2.28–2.36 (1H, m), 1.20–2.02 (9H, m), 1.35 (3H, s, H-14), 0.92–1.06 (1H, m), 0.93 (3H, d, J=5.99 Hz, H-15), 0.78 (3H, J=7.13 Hz, H-16); $\delta_c$: 174.20, 104.09, 91.92, 90.84, 90.04, 51.74, 51.27, 46.88, 45.46, 37.29, 36.02, 34.04, 28.91, 25.76, 24.66, 21.45, 20.10, 13.31; m/z (CI, NH$_3$) 402 (M$^+$+1, 100), 373 (30), 356 (64), 342 (16), 356 (20); Anal. Calc. for $C_{19}H_{33}NO_5S$: C, 56.84; H, 7.78; N, 3.49; found: C, 56.83; H, 7.82; N, 3.37.

EXAMPLE 8

Preparation of 10α-(4'-benzylpiperazin-1'-yl)-10-deoxo-10-dihydroartemisinin (Formula I: Y=4'-benzyl-1'-piperazinyl)

Reaction of the bromide prepared from 10β-(trimethylsiloxy)dihydroartemisinin (356 mg, 1.00 mmol) as described in Example 3 (b) with 1-benzylpiperazine (212.1 µl, 1.22 mmol) afforded 10α-(4'-benzylpiperazin-1'-yl)-10-deoxo-10-dihydroartemisinin (144.3 mg, 40%) as a white solid after flash chromatography (40% ethyl acetate/hexane). M.p. 105–106° C.; $[\alpha]_D^{20}$ +10.3° (c. 0.909 CHCl 3); $v_{max}$ (film): 2954, 2920, 2860, 2802, 1494, 1454, 1376, 1344, 1294, 1270, 1204, 1132, 1114, 1062, 1042, 1016, 986, 942, 924, 880, 852, 824, 738, 694 cm$^{-1}$; $^1$H NMR (300 MHz, CDCl$_3$) $\delta_H$ 7.43–7.30 (5H, m, Ar—H), 5.35 (1H, S, H-12), 4.10 (1H, d, J=10.2 Hz, H-10), 3.62 (1H, d, J=13.1 Hz, benzylic-H), 3.55 (1H, d, J=13.1 Hz, benzylic-H), 3.11–3.06 (2H, m), 2.80–2.70 (2H, m), 2.70–2.30 (7H, m), 2.15–2.02 (1H, m), 2.02–1.85 (1H, m), 1.85–1.70 (2H, m), 1.70–1.20 (9H, m), 1.20–1.00 (4H, m), 0.88 (3H, d, J=7.2 Hz, 6-methyl) ppm; $^{13}$C NMR (76 MHz, CDCl$_3$) $\delta_c$ 138.3, 129.13, 128.1, 126.9, 103.8, 91.6, 90.4, 80.3, 63.1, 53.5, 51.7, 45.9, 37.4, 36.3, 34.3, 28.5, 26.0, 24.5, 21.6, 20.3, 13.4 ppm; MS (CI, CH$_4$) m/e 443 (M$^+$+1, 10). Anal. Calcd. for $C_{26}H_{18}N_2O_4$: C, 7056, H, 8.65, N, 6.33; Found: C, 70.24, H, 8.67, N, 6.28.

EXAMPLE 9

Preparation of 10α-(2'-furyl)-10-deoxo-10-dihydroartemisinin (Formula I: Y=2-furyl)

Method 1:

To a solution of dihydroartemisinin (284 mg, 1.0 mmol) in dichloromethane (10 mL) at 20° C. was added trichloroacetonitrile (2.0 mL, 20.0 mmol) and one drop of 1,8-diazabicyclo[5.4.0]undecane. The mixture was stirred at 20° C. for 2 hours after which it was concentrated in vacuo at 20° C. The residue was then taken up in dichloromethane (10 mL) at 0° C. and cooled to −40° C. The solution was treated sequentially with furan (1.09 mL, 15.0 mmol) and boron trifluoride diethyl etherate (123 μl, 1.0 mmol), and the resulting mixture was stirred at −40° C. for another 30 min. The mixture was quenched with saturated $NaHCO_3$ solution and extracted with dichloromethane (2×10 mL). The extracts were dried ($MgSO_4$) and concentrated in vacuo. The residue was purified by flash chromatography ($SiO_2$; 15% ethyl acetate/hexanes) to give the captioned compound (11.0 mg, 3.3%) as a colourless oil. Analytical sample was obtained from recrystallization from hexanes.

Method 2:

(a) Preparation of 10β-benzoyloxy-10-dihydroartemisinin (10β-dihydroartemisinyl benzoate)

To a solution of dihydroartemisinin (568 mg, 2.00 mmol) and benzoic acid (244 mg, 2.00 mmol) in tetrahydrofuran at 0° C. under nitrogen was added triphenylphosphine (524 mg, 2.00 mmol) and diethyl azodicarboxylate (ml). The mixture was allowed to warm to room temperature and stirred overnight. The solution was concentrated in vacuo. Flash chromatography ($SiO_2$; 10% ethyl acetate/hexanes) gave 10-dihydroartemisinyl benzoate as a white solid (419 mg, 53%). M.p. 151.4–153.0° C.; $[\alpha]_D^{20}$ +119° (c 0.19/ $CHCl_3$); $\nu_{max}$ (film): 2942, 2872, 1724, 1452, 1378, 1268, 1176, 1114, 1064, 1024, 976, 902, 858, 832, 754, 712; $\delta_H$ 7.43–8.03 (5H, m, Ar—H), 6.52 (1H, d, J 3.43, H-10), 5.53 (1H, s, H-12), 2.91–3.01 (1H, m, H-9), 2.42 (1H, ddd, J=17.4, 13.3, 3.91 Hz), 1.33–2.10 (10H, m), 1.45 (3H, s, H-14), 1.02 (3H, d, J=6.11 Hz, H-15), 0.98 (3H, d, J=7.35 Hz, H-14); $\delta_c$: 165.31, 133.03, 12.96, 129.48, 128.39, 104.30, 95.29, 88.66, 88.63, 80.42, 52.27, 43.84; 37.44, 36.10, 34.43, 29.98, 25.76, 24.50, 24.25, 20.14, 12.50; m/z (EI): 388 ($M^+$).

(b) Preparation of 10α-(2'-furyl)-10-deoxo-10-dihydroartemisinin (Formula I: Y=2-furyl)

A solution of 10α-benzoyloxy-10-dihydroartemisinin (193 mg, 0.50 mmol) in dichloromethane (5 mL) at −45° C. was treated sequentially with furan (542 μl, 7.5 mmol) and boron trifluoride diethyl etherate (123 μl, 1.0 mmol). The resulting mixture was stirred at −45° C. for another 1 hr. The mixture was quenched with saturated $NaHCO_3$ solution and extracted with dichloromethane (3×10 mL). The extracts were dried ($MgSO_4$) and concentrated in vacuo. The residue was purified by flash chromatography ($SiO_2$; 15% ethyl acetate/hexanes) to give the captioned compound (53.7 mg, 32%) as a colourless oil. M.p. 96–97° C.; $^1H$ NMR (300 MHz, $CDCl_3$) $\delta_H$ 7.38 (1H, m, H-5'), 6.34–6.30 (2H, m, H-3' & H-4'), 5.38 (1H, s, H-12), 4.46 (1H, d, J=10.9 Hz, H-10), 2.84 (1H, m), 2.60–2.20 (2H, m), 2.20–1.20 (9H, m), 1.20–0.80 (6H, m), 0.62 (3H, d, J=7.2 Hz, 6-methyl) ppm; $^{13}C$ NMR (76 MHz, $CDCl_3$) $\delta_c$ 153.2, 142.0, 110.0, 108.3, 104.2, 92.2, 80.4, 76.6, 71.1, 52.0, 45.7, 37.4, 36.3, 34.1, 31.5, 26.1, 24.7, 21.3, 20.3, 13.7 ppm; MS (CI, $CH_4$) m/e 335 ($M^+$+1, 43).

EXAMPLE 10

Preparation of 10α-(Pyrrol-2'-yl)-10-deoxo-10-dihydroartemisinin (Formula I: Y=2-pyrrolyl)

A solution of 10β-benzoyloxy-10-deoxoartemisinin (700.8 mg, 1.80 mmol) prepared as described in Example 9, method 2 (a) in dichloromethane (30 mL) at −50° C. was treated sequentially with pyrrole (624 μl 1, 9.00 mmol) and boron trifluoride diethyl etherate (332 μl, 2.70 mmol), and then stirred at −50° C. for 1 hr. The mixture was quenched with saturated $NaHCO_3$ solution, and extracted with dichloromethane (3×10 mL). The extracts were dried ($MgSO_4$) and concentrated in vacuo. The residue was purified by flash chromatography ($SiO_2$; 30% diethyl ether/hexanes) to give the captioned compound (486.6 mg, 81%) as a colourless oil. $[\alpha]_D^{20}$+198.70 (c 0.105 $CHCl_3$); $\nu_{max}$ (film): 2924, 2854, 1460, 1376, 1066, 1024, 722 $cm^{-1}$; $^1H$ NMR (300 MHz, $CDCl_3$) $\delta_H$ 8.80 (1H, br s, NH), 6.71 (1H, m, H-5'), 6.04 (2H, m, H-3' & H-4'), 5.39 (1H, s, H-12), 4.47 (1H, d, J=10.8 Hz), 2.58 (1H, m), 2.50–2.10 (2 Y, m), 2.10–1.95 (1H, m), 1.93 (1H, m), 1.80–1.68 (2H, m), 1.68–1.15 (7H, m), 1.15–0.80 (4H, m), 0.93 (3H, d, J=7.1 Hz, 6-methyl) ppm; $^{13}C$ NMR (76 MHz, $CDCl_3$) $\delta_c$ 129.9, 117.6, 107.2, 106.7, 104.1, 91.9, 80.5, 71.9, 60.2, 51.8, 45.7, 37.2, 36.2, 34.0, 32.9, 25.9, 24.6, 21.2, 20.1, 14.0, 13.9 ppm; MS (CI, butane) m/e 334 ($M^+$+1, 100). Anal. Calcd. for $C_{19}H_{27}NO_4$: C, 68.44, H, 8.16, N, 4.20; Found: C, 68.77, H, 8.56, N, 3.85.

EXAMPLE 11

Preparation of 10α-(4'-Benzyl-4'-methylpiperazinium-1'-yl)-10-deoxo-10-dihydroartemisinin Iodide Salt (Formula I: Y=4'-benzyl-4'-methylpiperazinium-1-yl)

A solution of 10α-(4'-benzylpiperazin-1'-yl)-10-deoxo-10-dihydroartemisinin (272 mg, 0.62 mmol) prepared as described in Example 8 above in a mixture of dichloromethane (1.8 mL) and diethyl ether (5.4 mL) under nitrogen atmosphere at 0° C. was treated dropwise with iodomethane (36.7 μl, 0.59 mmol). The mixture was agitated and allowed to warm to 20° C. gradually overnight. The precipitate was collected and washed with diethyl ether (2×5 mL) and dried in high vacuum. It was further purified by recrystallization from methanol/diethyl ether to yield rectangular-plate shaped crystals (87 mg, 24%). M.p. 159–161° C.; $[\alpha]_D^{20+18.4°}$(c 0.436 $CHCl_3$); $\nu_{max}$ (film): 3448, 2928, 2196, 1457, 1378, 1210, 1133, 1099, 1041, 982, 918, 880, 852, 828, 766, 732, 642 $cm^{-1}$; $^1H$ NMR (300 MHz, $CDCl_3$) $\delta_H$ 8.00–7.60 (2H, d, J=6.2 Hz, H-2"& H-6"), 7.60–7.35 (3H, m, Ar—H), 5.32 (1H, s, H-12), 5.25–5.05 (2H, m, benzylic-H), 4.13 (1H, 6, J=10.2 Hz, H-10), 3.95–3.55 (4H, m), 3.55–2.90 (9, H), 2.65–2.20 (2H, m), 2.20–1.15 (14H, m), 1.15–0.87 (4H, m), 0.80 (3H, d, J=6.9 Hz, 6-methyl) ppm; $^{13}C$ NMR (76 MHz, $CDCl_3$) $\delta_c$ 133.4, 130.6, 129.1, 126.5, 104.0, 91.5, 90.1, 80.1, 67.4, 59.5, 59.3, 51.5, 45.5, 37.2, 36.1, 34.0, 28.4, 25.9, 24.5, 21.5, 20.1, 13.3 ppm.

EXAMPLES 12 to 61

By processes similar to those described in Examples 1 to 11 above, further compounds according to the invention were prepared as detailed in Table I below. In this table, the compounds are identified by reference to formula I.

TABLE I

| Ex. No. | Y | R¹ | R² | Physical data |
|---|---|---|---|---|
| 12 | 2,4,6-(—OCH$_3$)$_3$ phenyl (mixture of isomers) | — | — | White foam. $[\alpha]_D^{20.5}$ +49.51°(c. 0.053 in CHCl$_3$); $\nu_{max}$(Neat): 2936, 2872, 1608, 1496, 1456, 1420, 1374, 1330, 1278, 1224, 1204, 1152, 1120, 1050, 1040, 974, 954, 930, 902, 880, 856, 834, 814, 734, 702 cm$^{-1}$: $\delta_H$ 6.10–6.18(2H, m, Ar—H), 5.46(1H, s, H12), 5.38(1H, s, H-12'), 5.31(1H, d, J=10.4Hz, H-10), 5.07(1H, d, J=10.9Hz, H-10'), 3.88, 3.81, 3.80, 3.76 (OMe), 3.36–3.42(1H, m), 2.35–2.41(1H, m), 1.05–2.15(10H, m), 1.63(3H, s, H-14), 1.39(3H, s, H-14'), 0.99(3H, d, J=6.27Hz, H-16'), 0.88–0.93(3H, m, H-15 & H-16), 0.58(3H, d, J=7.26Hz, H-15'); m/z(CI, NH$_3$) 452(M+NH$_4^+$, 4%), 436(16), 435(M$^+$+1, 12), 419(100), 389 (74), 347(28). Anal. Calc. for C$_{24}$H$_{34}$O$_7$: C, 66.36; H, 7.83; Found: C, 66.42; H, 7.89 |
| 13 | 2-naphthyl (10β-isomer) | — | — | White solid. M.p. 145–146° C.; $[\alpha]_D^{20}$: −67.8°(c 0.027/CHCl$_3$); $\nu_{max}$(film) 2950, 2874, 1510, 1452, 1376, 1208, 1106, 1074, 1040, 1010, 954, 936, 886, 854, 824, 786, 750; $\delta_H$ 7.80–7.85(5H, m, Ar—H), 7.42–7.51(3H, m, Ar—H), 5.93(1H, d, J=6.59Hz, H-10), 5.67(1H, s, H-12), 2.81–2.94(1H, m, H-9), 2.33–2.48(1H, m), 0.86–2.13(10H, m), 1.42(3H, s, H-14), 1.02(1H, d, J=6.09Hz, H-16), 0.55 (1H, d, J=7.66Hz, H-15); $\delta_c$ 134.85, 127.82, 127.42, 127.12, 125.65, 125.17, 124.84, 124.26, 90.92, 73.04, 51.48, 43.44, 37.48, 36.64, 34.15, 32.10, 25.69, 24.89, 24.77, 19.85, 13.65; m/z(CI, CH$_4$) 395(M$^+$+1, 16%), 394(M+, 32), 362(44), 349(84), 331(16), 304(20), 291(26), 182(100), 168(60). Anal. Calcd. for C$_{25}$H$_{30}$O$_6$: C, 76.11; H, 7.66; found: C, 76.24; H, 7.69. |
| 14 | 2-OCH$_3$ phenyl (10β-isomer) | — | — | Colourless oil. $\delta_H$ 6.83–7.50(4H, m, Ar—H), 5.94(1H, d, J=6.65Hz, H-10), 5.58(1H, s, H-12), 3.84(3H, s, OCH$_3$), 2.86–2.99(1H, m, H-9), 2.30–2.40(1H, m), 1.19–2.11(10H, m), 1.39(3H, s, H-14), 1.01(1H, d, J=5.77Hz, H-16), 0.43(1H, d, J=7.64Hz, H-15); $\delta_c$ 134.85, 127.00, 126.37, 120.02, 109.19, 90.86, 68.63, 55.19, 51.30, 43.39, 37.53, 36.72, 34.21, 29.87, 25.68, 24.97, 24.75, 19.83, 13.45; m/z(CI, CH$_4$) 375(M$^-$+1, 12%), 374(M$^+$, 16), 342(100), 329(48), 311(14), 284(28), 182(56), 148(76), 137(60), 121(48). Anal. Calc. for C$_{22}$H$_{30}$O$_3$: C, 70.56; H, 8.07; Found C, 70.78; H, 8.28 |
| 15 | —NR¹R² (10α-isomer) | —H | phenyl | White solid. M.p. 159–160° C.; $[\alpha]_D^{20}$ −51.4°(c 0.35/CHCl$_3$); $\nu_{max}$(film) 3348, 2924, 2872, 1604, 1502, 1444, 1376, 1314, 1270, 1196, 1152, 1116, 1098, 1040, 1012, 994, 944, 926, 878, 856, 826, 748, 690; $\delta_H$ 7.17–7.22(2H, m, Ar—H), 6.75–6.87(3H, m, Ar—H), 5.45(1H, s, H-12), 4.85(1H, dd, J=9.86, 9.81 Hz, H-10), 4.32(1H, d, J=9.81Hz, NH), 2.49–2.61(1H, m, H-9), 2.35–2.45(1H, m), 2.00–2.08(1H, m), 1.74–1.92(4H, m), 1.26–1.65(7H, m), 1.42(3H, s, H-14), 1.05–1.10(1H, m), 1.01(3H, d, J=6.18 Hz, H-16), 0.95(3H, d, J=7.18Hz, H-15); $\delta_c$ 128.99, 118.56, 114.02, 91.08, 80.70, 80.39, 51.71, 45.76, 37.18, 36.26, 34.03, 32.71, 25.97, 24.60, 21.79, 20.17, 13.80; m/z(CI, CH$_4$) 360(M$^+$+1, 56%), 359 (M+, 56), 342(98), 324(100), 314(100), 296(98), 267(50), 249(22), 221(80), 163(40), 133(100), 94(38). Anal. Calc. for C$_{21}$H$_{25}$NO$_4$: C, 70.17; H, 8.13; N, 3.90; Found: C, 70.25; H, 8.24; N, 3.73 |

TABLE I-continued

| Ex. No. | Y | R$^1$ | R$^2$ | Physical data |
|---|---|---|---|---|
| 16 | —NR$^1$R$^2$ (10α-isomer) | —H | 4-F phenyl | White solid. M.p. 170.1° C.; ν$_{max}$(Nujol): 3358(ν$_{NH}$), 2924, 2854, 1512, 1460, 1378, 1264, 1216, 1194, 1116, 1099, 1046, 1022, 942, 924, 880, 846, 832, 810, 780 cm$^{-1}$, δ$_H$ 6.66–6.92(4H, m, Ar—H), 5.44(1H, s, H-12), 4.76(1H, dd, J=10.0, 10.0Hz, H-10), 4.32(1H, d, J=10.0Hz, NH), 2.49–2.61(1H, m, H-9), 2.40(1H, ddd, J=17.3, 13.4, 3.93Hz), 2.05(1H, ddd, J=14.6, 4.79, 3.07Hz), 1.05–1.97(9H, m), 1.42(3H, s, H-14), 1.00(3H, d, J=6.11Hz, H-16), 0.95(3H, d, J=7.18Hz, H-15); δ$_c$ 141.95, 115.34(d, J=17.7 Hz), 115.15(d, J=2.69Hz), 104.13, 91.10(d, J=2.22Hz), 81.41, 80.41, 51.69, 45.73, 37.29, 36.25, 34.01, 32.60, 25.94, 24.60, 21.79, 20.17, 13.81; m/z (CI, CH$_4$) 378(M$^+$+1, 44%), 377(M$^+$, 100), 358(70), 314(14), 267(26), 221(18), 163(34), 151(42), 111(6). Anal. Calc. for C$_{31}$H$_{28}$FNO$_4$: C, 66.82; H, 7.48; N, 3.71; Found C, 67.06; H, 7.60; N, 3.51 |
| 17 | —NR$^1$R$^2$ (10α-isomer) | —H | 4-Cl phenyl | White solid. M.p. 179.0° C.; [α]$_D^{20}$ -63.5° (c 0.20/CHCl$_3$); ν$_{max}$(film): 3346, 2926, 2874, 1604, 1514, 1494, 1454, 1378, 1268, 1196, 1152, 1094, 1040, 1012, 992, 944, 926, 878, 818, 756; δ$_H$ 7.09–7.14(2H, m, Ar—H), 6.66–6.71(2H, m, Ar—H), 5.44(1H, s, H-12), 4.78(1H, brs, H-10), 4.42(1H, brs, NH), 2.49–2.61(1H, m, H-9), 2.40 (1H, ddd, J=17.4, 13.5, 3.98Hz), 2.05 (1H, ddd, J=14.6, 4.78, 3.12Hz), 1.05–1.97(9H, m), 1.41(3H, s, H-14), 1.00(3H, d, J=6.12Hz, H-16), 0.94 (3H, d, J=7.18Hz, H-15); δ$_c$ 144.31, 128.76, 123.20, 115.28, 104.15, 91.09, 80.76, 80.38, 51.66, 45.67, 37.28, 36.23, 33.99, 32.56, 25.93, 24.59, 21.78, 20.16, 13.73; m/z(CI, CH$_4$) 393(M$^+$+1, 16%), 376 (8), 347(20), 330(16), 267(10), 221 (16), 167(100), 127(8). Anal. Calc. for C$_{31}$H$_{28}$ClNO$_4$: C, 64.03; H, 7.16; N, 3.55; Found C, 64.16; H, 7.40; N, 3.45. |
| 18 | —NR$^1$R$^2$ (10α-isomer) | —H | 4-Br phenyl | White solid. M.p. 183.1° C.; [α]$_D^{20}$ -60.0° (c 0.23/CHCl$_3$); ν$_{max}$(film) 3346, 2924, 2872, 1598, 1514, 1492, 1452, 1378, 1268, 1196, 1152, 1122, 1094, 1040, 1012, 992, 926, 878, 816, 756; dH 7.20–7.25(2H, m, Ar—H), 6.61–6.66(2H, m, Ar—H), 5.44(1H, s, H-12), 4.78(1H, dd, J=10.0, 9.95 Hz, H-10), 4.48(1H, d, J=10.0Hz, NH), 2.49–2.61(1H, m, H-9), 2.40(1H, ddd, J=14.0, 13.7, 3.87Hz), 1.05–2.08(10H, m), 1.41(3H, s, H-14), 1.00(3H, d, J=6.07Hz, H-16), 0.94(3H, d, J=7.15Hz, H-15); δ$_c$ 144.79, 131.61, 115.76, 110.32, 104.17, 91.09, 80.65, 80.39, 51.67, 45.67, 37.29, 36.24, 33.99, 32.54, 25.92, 24.60, 21.78, 20.17, 13.71; m/z(CI, CH$_4$) 439(M$^+$+1, 12%), 422(14), 392(100), 376 (36), 267(14), 221(50), 154(34). Anal. Calc. for C$_{31}$H$_{21}$BrNO$_4$: C, 57.54; H, 6.44; N, 3.19; Found: C, 57.81; H, 6.64; N, 3.14. |
| 19 | —NR$^1$R$^2$ (10α-isomer) | —H | 4-I phenyl | White solid. [α]$_D^{20}$ -68.8°(c 0.16/CHCl$_3$); ν$_{max}$(film) 3346, 2924, 1592, 1510, 1454, 1378, 1268, 1196, 1040, 994, 926, 878, 818, 754; δ$_H$ 7.36–7.41(2H, m, Ar—H), 6.51–6.56(2H, m, Ar—H), 5.43(1H, s, H-12), 4.78(1H, dd, J=10.0, 9.97Hz, H-10), 4.56(1H, d, J=10.0Hz, NH), 2.34–2.56(2H, m, H-9), 1.05–2.08 (10H, m), 1.41(3H, s, H-14), 1.00(3H, d, J=6.04Hz, H-16), 0.93(3H, d, J=7.13Hz, H-15); δ$_c$ 145.46, 137.45, 116.35, 104.18, 91.09, 80.46, 79.59, 51.66, 45.66, 37.29, 36.25, 34.00, 32.50, |

TABLE I-continued

| Ex. No. | Y | $R^1$ | $R^2$ | Physical data |
|---|---|---|---|---|
| | | | | 25.91, 24.61, 21.79, 20.19, 13.71; m/z (CI, CH$_4$) 486(M$^+$+1, 4%), 485(M$+$, 6), 468 (12), 440(100), 422(34), 267(6), 259 (20), 221(20). Anal. Calc. for C$_{21}$H$_{24}$INO$_4$: C, 51.97; H, 5.81; N, 2.89; Found: C, 52.22; H, 5.83; N, 2.57. |
| 20 | —NR$^1$R$^2$ (10α-isomer) | —H | 4-biphenyl | White solid. [α]$_D^{20}$ −76.5°(c 0.51/CHCl$_3$); ν$_{max}$(film) 3348, 2924, 2872, 1614, 1528, 1488, 1446, 1378, 1268, 1268, 1196, 1152, 1128, 1040, 1012, 992, 926, 878, 826, 760, 698; δ$_H$ 7.25–7.58(7H, m, Ar—H), 6.82–6.87(2H, m, Ar—H), 5.49(1H, s, H-12), 4.90(1H, dd, J=9.85, 9.85 Hz, H-10), 4.50(1H, d, J=9.85Hz, NH), 2.36–2.62(2H, m), 1.07–2.09(10H, m), 1.44(3H, s, H-14), 1.02(3H, d, J=6.12 Hz, H-16), 0.98(3H, d, J=7.17Hz, H-15); δ$_c$ 145.22, 141.16, 131.53, 128.45, 127.71, 126.29, 125.98, 114.30, 104.14, 91.14, 80.67, 80.42, 51.72, 45.76, 37.30, 36.27, 34.04, 21.68, 25.98, 24.62, 21.81, 20.19, 13.81; m/z(CI, CH$_4$): 436(M$^+$+1, 2%), 412(100), 395(42), 379(8), 284 (2), 267(2), 170(2). Anal. Calc. for C$_{27}$H$_{33}$NO$_4$: C, 74.45; H, 7.64; N, 3.22; Found: C, 73.51; H, 7.67; N, 3.12. |
| 21 | —NR$^1$R$^2$ (10α-isomer) | —H | benzyl | White solid. [α]$_D^{20}$ −26.7°(c 0.15/CHCl$_3$); ν$_{max}$(film) 3348, 2924, 2870, 1452, 1376, 1158, 1116, 1056, 1042, 1014, 992, 942, 926, 878, 828, 736, 700; δ$_H$ 7.21–7.42 (5H, m, Ar—H), 5.32(1H, s, H-12), 4.17 (1H, d, J=13.9Hz, H-1'), 4.13(1H, d, J=9.63Hz, H-10), 3.97(1H, d, J=13.9 Hz, H-1'), 2.29–2.45(2H, m), 2.29(1H, brs, NH), 2.01–2.09(1H, m), 1.86–1.95 (1H, m), 1.65–1.78(2H, m), 1.44–1.59 (2H, m), 1.48(3H, s, H-14), 1.22–1.40 (3H, m), 0.91–1.09(1H, m), 0.97(3H, d, J=5.94Hz, H-16), 0.96(3H, d, J=7.14 Hz, H-15); δ$_c$ 140.82, 128.03, 127.84, 126.45, 103.91, 91.39, 85.68, 80.65, 51.69, 40.21, 45.86, 37.24, 36.29, 34.07, 32.77, 26.07, 24.63, 21.73, 30.19, 14.12; m/z(CI, CH$_4$) 374(M$^+$+1, 100%), 356(54), 338(42), 328(38), 309(12), 253(16), 221(10), 119(16). Anal. Calc. for C$_{22}$H$_{31}$NO$_4$: C, 70.75; H, 8.37; N, 3.75; Found: C, 70.78; H, 8.82; N, 3.75. |
| 22 | —NR$^1$R$^2$ (10α-isomer) | —H | 2-F benzyl | White solid. M.p. 47.4–48.7° C., [α]$_D^{20}$ −16.9°(c 1.46/CHCl$_3$); ν$_{max}$(film) 3336, 2924, 2872, 1584, 1486, 1454, 1376, 1226, 1196, 1158, 1116, 1056, 1042, 1014, 994, 926, 878, 826, 756; δ$_H$ 6.99–7.50(4H, m, Ar—H), 5.34(1H, s, H-12), 4.21(1H, d, J=14.5Hz, H-1'), 4.15(1H, d, J=6.72 Hz, H-10), 3.99(1H, d, J=14.5Hz, H-1'), 2.35–2.45(2H, m), 0.90–2.08(10H, m), 1.47(3H, s, H-14), 0.98(3H, d, J=5.99Hz, H-16), 0.94(3H, d, J=7.16Hz, H15); δ$_c$ 129.63(d, J=4.79Hz), 127.94 (d, J=8.05Hz), 123.64(d, J=3.40 Hz), 114.89(d, J=21.6Hz), 103.90, 91.35, 86.03, 80.59, 51.69, 45.86, 41.96 (d, J=3.53Hz), 37.26, 36.28, 34.08, 32.66, 26.02, 24.62, 21.72, 20.17, 14.00; δ$_f$ −120; m/z(CI, CH4) 392(M$^+$+1, 24%), 374(46), 346(100), 328(34), 267(2), 221(4), 209(6), 165(82), 154(50), 109(42). Anal. Calcd. for C$_{22}$H$_{30}$NO$_4$F: C, 67.50; H, 7.72; N, 3.58; found C, 67.75, H, 7.92; N, 3.49. |
| 23 | —NR$^1$R$^2$ (10α-isomer) | —H | 3,5-(CF$_3$)$_2$ benzyl | Colourless oil. M.p. 51.0–52.8° C.; [α]$_D^{20}$ −27°(c 0.027 CHCl$_3$) δ$_H$ 7.88(2H, brs, Ar—H), 7.56(1H, brs, Ar—H), 5.31(1H, s, H-12), 4.24(1H, d, J=15.1Hz, H-1'), 4.12(1H, d, J=15.1Hz, H-1'), 4.06(1H, d, J=9.82Hz, H-10), 2.34–2.45(2H, m), |

TABLE I-continued

| Ex. No. | Y | R¹ | R² | Physical data |
|---|---|---|---|---|
| | | | | 0.90–2.09(10H, m), 1.47(3H, s, H-14), 0.98(3H, d, J=7.26Hz, H-15), 0.97(3H, d, J=4.94Hz, H16); $\delta_F$ −64.1; m/z(CI, CH$_4$) 510(M$^+$+1, 48%), 490(100), 464(74), 441(38), 283(24), 267(30), 244(10), 221(20), 163(22). Anal. Calc. for C$_{21}$H$_{29}$NO$_4$F$_6$: C, 56.58; H, 5.74; N, 2.75; Found: C, 56.75; H, 5.76; N, 2.70. |
| 24 | —NR¹R² (10α-isomer) | —H | —$^n$C$_3$H$_7$ | White solid. M.p. 96.1–97.3° C. (changed colour before melting); $[\alpha]_D^{20}$ +24.8°(c 0.33/CHCl$_3$); $\nu_{max}$(film) 3304, 2952, 2924, 2870, 1492, 1454, 1378, 1208, 1160, 1118, 1042, 1012, 974, 942, 922, 878, 844, 828, 754; $\delta_H$ 5.31(1H, s, H-12), 4.11(1H, d, J=9.78Hz, H-10), 2.95(1H, ddd, J=11.4, 8.07, 6.55Hz, CH$_2$NH), 2.61(1H, ddd, J=11.4, 8.07, 6.45Hz, CH$_2$NH), 2.26–2.43(2H, m), 2.03(1H, ddd, J=14.5, 4.54, 2.49Hz), 1.84–1.93(1H, m), 1.00–1.83(10H, m), 1.44(3H, s, H-14), 0.97(3H, d, J=6.10Hz, H-16), 0.92 (3H, t, J=7.36Hz, CH3), 0.89(3H, d, J=7.18Hz, H-15); $\delta_c$ 103.82, 91.34, 86.17, 51.69, 46.27, 45.88, 37.27, 36.27, 34.10, 32.49, 26.04, 24.61, 23.49, 21.72, 20.19, 14.03, 11.62; m/z(CI, CH$_4$) 326 (M$^+$+1, 100%), 308(56), 280(48), 221 (16), 163(18). Anal. Calcd. for C$_{18}$H$_{22}$NO$_4$: C, 66.43; H, 9.60; N, 4.36; Found: C, 66.17, H, 9.68; N, 4.20. |
| 25 | morpholino (10α-isomer) | — | — | White solid. M.p. 121.2° C.; $[\alpha]_D^{20}$ +15.3° (c 0.30/CHCl$_3$); $\nu_{max}$(film) 2924, 2050, 1450, 1376, 1294, 1258, 1202, 1150, 1110, 1056, 984, 930, 880, 846, 826, 744; $\delta_H$ 5.29(1H, s, H-12), 3.99(1H, d, J=10.23Hz, H-10), 3.63–3.76(4H, m, O(CH$_2$)$_2$), 2.96–3.03(2H, m, CH$_2$NCH$_2$), 2.64–2.71(2H, m, CH$_2$NCH$_2$), 2.53–2.61(1H, m, H-9), 2.31–2.41(1H, m), 1.00–2.06 (10H, m), 1.41(3H, s, H-14), 0.96(3H, d, J=6.14Hz, H-16), 0.83(3H, d, J=7.18Hz, H-15); $\delta_c$ 103.74, 91.48, 90.51, 80.16, 67.25, 51.57, 47.52, 45.66, 37.25, 36.16, 34.14, 28.04, 25.84, 24.62, 21.50, 20.14, 13.25; m/z(EI) 353(M+, 6), 294 (4), 236(4), 221(16), 209(12), 163 (14), 127(32), 116(100), 88(24). Anal. Calcd. for C$_{19}$H$_{31}$NO$_5$: C, 64.56; H, 8.84; N, 3.96%; Found: C, 64.67; H, 9.10; N, 3.90. |
| 26 | —NR¹R² (10α-isomer) | —C$_2$H$_5$ | —C$_2$H$_5$ | White solid. $\delta_H$ 5.37(1H, s, H-12), 4.76 (d, J=7.54Hz, H-10), 2.80–3.03(4H, m, N(CH$_2$CH$_3$)$_2$), 2.29–2.44(1H, m, H-9), 0.94–1.89(11H, m), 1.53(3H, s, H-14), 1.14(6H, dd, J=7.20, 7.12Hz, N(CH$_2$CH$_3$)$_2$), 1.04(3H, d, J=7.23Hz, H-15), 0.91(3H, d, J=5.72Hz, H-16); $\delta_c$ 105.33, 96.11, 81.43, 51.68, 45.23, 41.48, 35.12, 34.52, 33.96, 29.56, 23.77, 22.24, 21.88, 18.52, 15.56, 11.50. m/z(CI, CH$_4$): 340(M$^+$+1, 52%), 251 (100), 221(26). |

TABLE I-continued

| Ex. No. | Y | R¹ | R² | Physical data |
|---|---|---|---|---|
| 27 | indolinyl 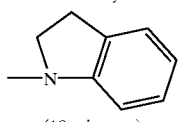 (10α-isomer) | — | — | White solid. M.p. 147.8–148.2° C.; $[\alpha]_D^{20}$ –11.6°(c 0.19/CHCl$_3$); $\nu_{max}$(film) 2926, 2872, 1606, 1488, 1462, 1376, 1258, 1200, 1158, 1126, 1040, 1010, 926, 880, 828, 746, 718; $\delta_H$ 7.03–7.09(2H, m, Ar—H), 6.60–6.71(2H, m, Ar—H), 5.44(1H, s, H-12), 4.98(1H, d, J=10.4Hz, H-10), 3.79(1H, apparent dt, J=10.4, 9.08Hz, ArCH$_2$), 3.56(1H, apparent dt, J=9.08, 4.36Hz, ArCH$_2$), 2.94–3.12(2H, m, NCH$_2$), 2.67–2.79(1H, m, H-9), 2.39(1H, ddd, J= 14.3, 13.3, 3.94Hz), 2.03(1H, ddd, J= 14.5, 4.73, 2.97Hz), 1.75–1.95(4H, m), 1.06–1.69(6H, m), 1.38(3H, s, H-14), 1.00(3H, d, J=6.17Hz, H-16), 0.94(3H, d, J=7.16Hz, H-15); $\delta_c$ 150.51, 130.18, 126.92, 124.57, 118.19, 107.47, 103.90, 91.46, 81.53, 80.05, 51.58, 45.61, 44.83, 37.28, 36.20, 34.12, 29.75, 27.99, 25.83, 24.61, 21.51, 20.16, 13.30; m/z(CI, CH$_4$) 386 (M$^+$+1, 100), 340(50), 326(14), 267(6). Anal. Calcd. for C$_{23}$H$_{31}$NO$_4$; C, 71.66; H, 0.10; N, 3.63; Found: C, 71.45; H, 8.07; N, 3.57. |
| 28 | 1, 2, 3, 4-tetrahydro-isoquinolinyl 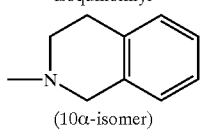 (10α-isomer) | — | — | White solid. M.p. 125.3–126.6° C.; $[\alpha]_D^{20}$ +14.7°(c 0.19/CHCl$_3$); $\nu_{max}$(film) 2924, 2870, 1452, 1376, 1278, 1200, 1154, 1130, 1100, 1040, 1014, 982, 926, 800, 826, 742; $\delta_H$ 7.07–7.15(4H, m, Ar—H), 5.36 (1H, s, H-12), 4.26(1H, d, J=10.2Hz, H-10), 4.20(1H, d, J=15.2Hz, ArCH$_2$N), 3.97(1H, d, J=15.2Hz, ArCH$_2$N), 3.26–3.36(1H, m, ArCH$_3$), 2.70–3.00(4H, m, 3H-CH$_2$CH$_2$N & 1H), 2.40(1H, ddd, J= 14.4, 13.6, 3.93Hz), 2.00–2.07(1H, m), 1.86–1.95(1H, m), 1.71–1.81(2H, m), 1.19–1.65(4H, m), 1.41(3H, s, H-14), 1.02–1.12(1H, m), 0.99(3H, d, J=6.09 Hz, H-16), 0.87(3H, d, J=7.19Hz, H-15); $\delta_c$ 135.74, 134.94, 128.55, 126.59, 125.45, 125.21, 103.76, 91.61, 90.60, 80.31, 51.64, 49.18, 45.82, 45.65, 37.29, 36.21, 34.20, 29.89, 28.66, 25.88, 24.67, 21.53, 20.19, 13.46; m/z(CI, CH$_4$) 400 (M$^+$+1, 100), 398(22), 354(54), 340 (20), 267(4), 162(44), 134(14). Anal. Calc. for C$_{24}$H$_{33}$NO$_4$: C, 72.15; H, 8.33; N, 3.51: Found: C, 71.98; H, 8.36; N, 3.36. |
| 29 | —NR¹R² (10α,1'S-isomer) | —H | —CH(CH$_3$)phenyl | White solid. M.p. 55.4–57.5° C.; $\delta_H$ 7.20–7.42(5H, m, Ar—H), 5.13(1H, s, H-12), 4.45(1H, q, J=6.62Hz, H-1'), 3.77(1H, d, J=9.79Hz, H-10), 2.23–2.43(2H, m), 2.03(1H, ddd, J= 14.5, 4.73, 3.08Hz), 0.96–1.88(9H, m), 1.48(3H, s, H-14), 1.31(3H, d, J=6.62 Hz, CH$_3$), 0.91(3H, d, J=5.94Hz, H-16), 0.91(3H, d, J=7.14Hz, H-15); $\delta_c$ 146.07, 128.01, 126.96, 126.39, 103.81, 91.38, 83.80, 80.70, 52.37, 51.71, 45.82, 37.08, 36.30, 33.95, 33.48, 26.11, 25.53, 24.57, 21.64, 20.14, 14.22; m/z(CI, CH$_4$) 388(M$^+$+1, 100%), 370(22), 342(64), 267(8), 221(10). Anal. Calc. for C$_{23}$H$_{33}$NO$_4$: C, 71.29; H, 8.58; N, 3.61; Found C, 71.20; H, 8.72; N, 3.62. |
| 30 | —NR¹R² (10α,1'R-isomer) | —H | —CH(CH$_3$)phenyl | White solid. $\delta_H$ 7.20–7.43(5H, m, Ar—H), 5.36(1H, s, H-12), 4.44(1H, q, J=6.41 Hz, H-1'), 4.31(1H, d, J=9.70Hz, H-10), 2.21–2.40(2H, m), 2.00–2.08(1H, m), 1.02–1.95(9H, m), 1.45(3H, s, H-14), 1.31(3H, d, J=6.41Hz, CH$_3$), 0.99(3H, d, J=6.18Hz, H-16), 0.93 (3H, d, J=7.16Hz, H-15); $\delta_c$ 147.01, |

TABLE I-continued

| Ex. No. | Y | R¹ | R² | Physical data |
|---|---|---|---|---|
| | | | | 128.06, 127.01, 126,59, 103.85, 91.33, 83.03, 80.56, 51.72, 51.51, 45.92, 37.29, 36.28, 34.14, 33.09, 26.01, 24.66, 22.35, 21.83, 20.21, 14.22; m/z(CI, $CH_4$) 388 ($M^+$+1, 100%), 370(56), 342(42), 309 (30), 267(18), 253(32), 221(20), 119(34). |
| 31 | —NR¹R² (10α,1'R-isomer) | —H | —CH(CO—OCH₃)phenyl | Colourless oil. $\nu_{max}$(Neat): 3342($\nu_{NH}$), 2926, 2827, 1742 ($\nu_{c-o}$, ester), 1602, 1494, 1452, 1376, 1246, 1198, 1158, 1130, 1042, 1014, 994, 928, 880, 844, 826, 736, 700 $cm^{-1}$; ¹H nmr (300MHz, $CDCl_3$) $\delta_H$ 7.21–7.50(5H, m, Ar—H), 5.13(1H, s, H-12), 4.94(1H, s, H-2'), 3.85(1H, d, J 9.81 Hz, H-10), 3.65(3H, s, OMe), 2.74(1H, br.s., NH), 2.35(1H, m, H-9), 1.05–2.07 (11H, m, H-2×2, H-3×2, H-4, H-5, H-6× 2, H-7×2, H-8), 1.47(3H, s, 1-$CH_3$), 0.90(6H, d×2, signals overlap, 5-$CH_3$, 9-$CH_3$) ppm; m/z(CI, $CH_4$) 432($M^+$+1, 96%), 386(100), 372(44), 312(14), 267(24), 221(28), 166(96). Anal. Calcd. for $C_{24}H_{33}NO_6$: C, 66.80; H, 7.71; N, 3.24; Found: C, 66.98; H, 7.53; N, 3.05. |
| 32 | —NR¹R² (10α,1'S-isomer) | —H | —CH(CO—OCH₃)phenyl | ¹H nmr (300MHz, $CDCl_3$) $\delta_H$ 7.28–7.51(5H, m, Ar—H), 5.22(1H, s, H-12), 5.04(1H, s, H-2'), 4.28(1H, d, J 9.81Hz, H-10), 3.68(3H, s, OMe), 2.57(1H, br.s., NH), 2.29–2.44(1H, m, H-9), 0.96–2.44(1H, m, H-2×2, H-3×2, H-4, H-5, H-6×2, H-7× 2, H-8), 1.43(3H, s, 1-$CH_3$), 0.97(3H, d, J 6.11Hz, H-15), 0.90(3H, d, J 7.16 Hz, H-16) ppm; m/z(CI, $CH_4$) 432($M^+$+1, 90%), 386(100), 372(50). |
| 33 | —NR¹R² (10α-isomer) | —H | 4-(CO—OCH₃)phenyl | White solid. M.p. 117.7–118.5° C.; $[\alpha]_D^{20}$ −84.1 (c 0.82/$CHCl_3$); $\nu_{max}$(film) 3344, 2948, 1710, 1608, 1528, 1434, 1378, 1270, 1178, 1110, 1040, 1012, 926, 878, 842, 768; $\delta_H$ 6.66–7.76(4H, m, Ar—H), 5.46 (1H, s, H-12), 5.06(1H, d, J=9.96Hz, NH), 4.88(1H, dd, J=9.89, Hz, H-10), 3.83(3H, s, OMe), 2.56–2.60(1H, m), 2.33–2.42(1H, m), 0.85–2.04(10H, m), 1.39(3H, s, H-14), 0.99(3H, d, J=6.09 Hz, H-15), 0.92(3H, d, J=7.11Hz, H-16; $\delta_c$: 167.06, 149.99, 131.04, 119.64, 113.01, 104.30, 91.20, 80.49, 80.02, 51.70, 51.40, 45.67, 37.34, 36.20, 34.04, 32.50, 25.92, 24.66, 21.84, 20.94, 20.22, 14.10, 13.67; m/z(CI, $CH_4$) 418($M^+$+1, 32), 400(6), 372(100), 358(8), 221(28), 152(26). Anal. Calc. for $C_{23}H_{31}NO_6$: C, 66.17; H, 7.48; N, 3.35; Found: C, 65.57; H, 7.57; N, 3.36. |
| 34 | —NR¹R² (α-isomer) | —H | cyclopentyl | White solid. M.p. 114.1–114.9° C.; $[\alpha]_D^{20}$: −1.6°(c 0.98/$CHCl_3$); $\nu_{max}$(film) 3314, 2950, 2870, 1446, 1376, 1198, 1154, 1114, 1098, 1042, 1014, 976, 944, 924, 878, 860, 826, 754; $\delta_H$: 5.29(1H, s, H-12), 4.08(1H, d, J=9.76Hz, H-10), 3.52–3.60 (1H, m, H-1'), 2.23–2.41(2H, m), 1.24–2.05(17H, m), 1.43(3H, s, H-14), 0.84–1.11(1H, m), 0.96(3H, d, J=6.15Hz, H-15), 0.85(3H, d, J=7.17Hz, H-16); $\delta_c$ 103.91, 91.44, 85.08, 80.77, 54.33, 51.84, 46.01, 37.38, 36.40, 34.23, 34.20, 33.11, 32.70, 26.17, 24.74, 23.63, 21.89, 20.31, 14.30; m/z(CI, $CH_4$) 352($M^+$+1, 14), 334(10), 306(100), 288(14), 251 (4), 221(4), 125(10); Anal. Calc. for $C_{20}H_{22}NO_4$: C, 68.34, H, 9.46; N, 3.98; Found: C, 67.89; H, 9.46; N, 3.92 |
| 35 | —NR¹R² (α-isomer) | —H | cyclohexyl | White solid. $\delta_H$ 5.28(1H, s, H-12), 4.17 (1H, d, J=9.69Hz, H-10), 2.93–3.00(1H, m H-1'), 2.16–2.41(2H, m), 0.84–2.03 (19H, m), 1.42(3H, s, H-14), 0.95(3H, d, J=6.11Hz, H-15), 0.85(3H, d, J=7.18 Hz, H-16); $\delta_c$ 103.87, 91.36, 83.36, |

TABLE I-continued

| Ex. No. | Y | R¹ | R² | Physical data |
|---|---|---|---|---|
| | | | | 80.70, 51.84, 50.94, 46.04, 37.36, 36.38, 34.58, 34.21, 33.18, 32.79, 26.29, 26.12, 24.75, 24.71, 24.27, 21.88, 20.29, 14.29, 14.39; m/z(CI, CH$_4$) 366(M$^+$+1, 10), 348 (10), 329(100), 318(12), 221(4), 139 (8); Anal. Calcd. for C$_{21}$H$_{25}$NO$_4$: C, 69.01; H, 9.65; N, 3.83; found: C, 68.85, H, 9.85; N, 3.80. |
| 36 | N-methyl-piperazino<br>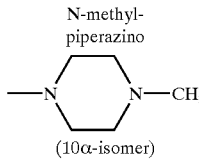<br>(10α-isomer) | — | — | Brownish yellow solid. M.p. 112–114° C.; [α]$_D^{20}$ +12.95°(c. 0.0149 in CHCl$_3$); ν$_{max}$ (Neat): 2934, 2872, 2792, 1454, 1376, 1286, 1226, 1192, 1162, 1132, 1102, 1054, 1014, 984, 926, 880, 830 cm$^{-1}$; $^1$H nmr (300 MHz, CDCl$_3$) δ$_H$ 5.26(1H, s, H-12), 4.02 (1H, d, J 10.20Hz, H-10), 3.03(2H, m, H-6'a, H-6'b), 2.70(2H, m, H-2'a, H-2'b), 2.59(1H, m, H-9), 2.30–2.50(5H, m, H-8, H-3'a, H-3'b, H-5'a, H-5'b), 2.28 (3H, s, N—Me), 1.18–2.05(10H, m, H-2a, H-2b, H-3a, H-3b, H-4, H-5, H-6a, H-6b, H-7a, H-7b), 1.36(3H, s, 1-CH$_3$), 0.94 (3H, d, J 6.12Hz, 9-CH$_3$), 0.80(3H, d, J 7.17Hz, 5-CH$_3$) ppm; δ$_c$ 104.46, 92.16, 90.96, 90.98, 56.18, 52.36, 46.82, 38.05, 36.96, 34.97, 29.16, 26.55, 25.46, 22.30, 20.96, 14.03; m/z(CI, CH$_4$) 367([M+1]$^+$, 100), 321([M-3CH$_3$]$^+$, 26), m/z(CI, CH$_4$) 367 ([M+1]$^+$, 100), 321([M-3CH$_3$]$^+$, 26). |
| 37 | 4-vinylphenyl<br>(10β-isomer) | — | — | White solid. [α]$_D^{22}$ −64.6°(c 0.028/CHCl$_3$); ν$_{max}$(film) 2948, 2876, 1630, 1512, 1452, 1406, 1376, 1200, 1116, 1074, 1010, 944, 904, 882, 844, 788, 756; δ$_H$: 7.37(2H, d, J=8.26Hz, Ar—H), 7.27(2H, d, J=8.26Hz, Ar—H), 6.71(1H, dd, J=17.62, 10.90Hz, vinyl-H), 5.69–5.76(2H, m, vinyl-H, H-10), 5.57(1H, s, H-12), 5.20(1H, d, J=10.90Hz, vinyl-H), 2.71–2.78(1H, m), 2.28–2.38(1H, m), 1.17–2.09(9H, m), 1.38 (3H, s, H-14), 0.83–0.99(1H, m), 0.98 (3H, d, J=5.74Hz, H-15), 0.54(3H, d, J=7.67Hz, H-16); δ$_c$: 140.91, 136.75, 135.74, 126.36, 125.72, 113.09, 102.40, 90.89, 81.24, 73.07, 51.58, 43.58, 37.58, 36.73, 34.26, 32.19, 25.80, 24.98, 24.80, 19.97, 13.75. Anal. Calcd. for C$_{29}$H$_{30}$O$_4$: C, 74.56; H, 8.16; found: C, 74.58; H, 8.26. |
| 38 | 4-Br phenyl<br>(10β-isomer) | — | — | White rectangular crystal. M.p. 156–159° C.; [α]$_D^{20.5}$ −45.14°(c 0.0216 in CHCl$_3$); ν$_{max}$ (Nujol): 2924, 1492, 1454, 1374, 1112, 1008, 942, 902, 882, 840, 780 cm$^{-1}$; $^1$H nmr (300MHz, CDCl$_3$) δH 7.43(2H, d, J 8.40 Hz, H-3', H-5'), 7.19(2H, d, J 8.40Hz, H-2', H-6'), 5.70(1H, d, J 6.60Hz, H-10), 5.55(1H, s, H-12), 2.72(1H, m, H-9), 2.33(1H, m, H-8), 1.19–2.10(10H, m, H-2a, H-2b, H-3a, H-3b, H-4, H-5, H-6a, H-6b, H-7a, H-7b), 1.40(3H, s, 1-CH$_3$), 0.98 (3H, d, J 5.70Hz, 9-CH$_3$), 0.48(3H, d, J 7.80Hz, 5-CH$_3$) ppm; m/z(CI, CH$_4$) 453 ([M(Br$^{83}$)+2CH$_4$]$^+$, 18), 451([M(Br$^{72}$)+ 2CH$_4$]$^+$, 20), 425([M(Br$^{81}$)+1]$^+$, 51), 423([M(Br$^{37}$)+1]$^+$, 53), 407(40), 405(32), 392(35), 390(48), 379(100), 377(88), 335(20), 333(28), 267(32), 221(41), 209(78), 191(78), 191(26), 163(59). |
| 39 | 4-Cl phenyl<br>(10β-isomer) | — | — | White rectangular crystal. M.p. 161–146° C.; [α]$_D^{20.5}$ −10.35°(c 0.0508 in CHCl$_3$); ν$_{max}$(Nujol): 2924, 1494, 1456, 1374, 1114, 1008, 942, 902, 840, 782 cm$^{-1}$; $^1$H nmr (300 MHz, CDCl$_3$) δ$_H$ 7.30(2H, d, J 8.16Hz, H-3', H-5'), 7.24(2H, d, J 8.16Hz, H-2', H-6'), 5.69(1H, d, J 6.60Hz, H-10), 5.55 (1H, m, H-12), 2.71(1H, m, H-9), 2.32(1H, m, H-8), 1.21–2.08(10H, m, H-2a, H-2b, H-3a, H-3b, H-4, H-5, |

TABLE I-continued

| Ex. No. | Y | R¹ | R² | Physical data |
|---|---|---|---|---|
| | | | | H-6a, H-6b, H-7a, H-7b), 1.36(3H, s, 1-CH$_3$), 0.98(3H, d, J 5.76Hz, 9-CH$_3$), 0.49(3H, d, J 7.68Hz, 5-CH$_3$) ppm; δ$_c$ 140.37, 132.75, 128.66, 128.31, 103.10, 91.64, 81.91, 73.28, 52.23, 44.16, 38.28, 37.41, 34.93, 32.80, 26.47, 25.53, 20.63, 14.36; m/z(CI, CH$_4$) 407([M(Cl$^{37}$)+2CH$_4$]$^+$, 6), 405([M(Cl$^{13}$)+2CH$_4$]$^+$, 5), 379([M(Cl$^{37}$)−1]$^+$, 97), 377([M(Cl$^{36}$)−1]$^+$, 100), 355(14), 333(26), 182(12). Anal. calc. for C$_{21}$H$_{27}$O$_4$Cl C, 66.57; H, 7.18; found C, 66.42; H, 7.05. |
| 40 | 9-anthryl 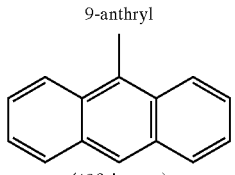 (10β-isomer) | — | — | White solid. δ$_H$ 9.00–9.05(1H, m, Ar—H), 8.31–8.41(2H, m, Ar—H), 7.05–8.04(2H, m, Ar—H), 7.39–7.57(4H, m, Ar—H), 7.23(1H, d, J=7.51Hz, H-10), 5.81(1H, s, H-12), 3.10–3.23(1H, m), 0.86–2.49(11H, m), 1.39(3H, s, H-14), 1.09(3H, d, J=5.81 Hz, H-15), 0.57(3H, d, J=7.72Hz, H-16); δ$_c$: 134.12, 131.70, 131.05, 130.88, 129.59, 129.19, 128.73, 128.47, 127.61, 126.05, 124.55, 124.51, 124.32, 123.71, 102.64, 91.22, 81.42, 72.62, 51.50, 44.18, 37.69, 36.87, 34.33, 33.02, 25.71, 25.09, 25.00, 19.94, 13.81. |
| 41 | 9-phenanthryl 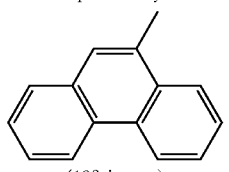 (10β-isomer) | — | — | White solid. M.p. 89–89.1° C.; [α]$_D^{20}$: −68.8°(c 0.016 CHCl$_3$); ν$_{max}$(film) 2922, 2874, 2362, 1498, 1450, 1376, 1246, 1220, 1110, 1040, 1010, 956, 930, 906, 886, 832, 794, 748, 726; δ$_H$: 8.68–8.81(2H, m, Ar—H), 7.91–8.10(3H, m, Ar—H), 7.57–7.72 (4H, m, Ar—H), 6.50(1H, d, J=6.54Hz, H-10), 5.75(1H, s, H-12), 3.06–3.19(1H, m), 2.37–2.48(1H, m), 2.00–2.16(3H, s), 1.73–1.84(2H, m), 0.86–1.60(5H, m), 1.41 (3H, s, H-14), 1.06(3H, d, J=5.67Hz, H-15), 0.39(3H, d, J=7.61Hz, H-16); δ$_c$: 135.21, 131.68, 130.14, 129.96, 129.59, 128.84, 126.66, 126.52, 126.04, 126.01, 123.84, 123.68, 123.19, 122.33, 102.47, 91.34, 81.42, 69.92, 51.45, 43.77, 37.71, 36.89, 34.27, 31.55, 25.79, 25.11, 24.95, 19.96, 13.22; m/z(CI, CH$_4$) 445(M$^+$+1, 22), 444(100), 398(40), 384(16), 352(16), 328(44), 267(6), 218(84), 203(48), 178 (60), 163(44), 138(70), 107(62). |
| 42 | 2-OCH$_3$ phenyl (10β-isomer) | — | — | White solid. M.p. 61° C.; [α]$_D^{20}$: −14.4°(c 0.049 CHCl$_3$); ν$_{max}$(film) 2928, 2874, 1590, 1492, 1462, 1374, 1284, 1240, 1178, 1110, 1102, 1052, 1010, 944, 882, 854, 754: δ$_H$ 6.83–7.50(4H, m, Ar—H), 5.94(1H, d, J=6.65, Hz, H-10), 5.58(1H, s, H-12), 3.84(3H, s, OC$\underline{H}_3$), 2.86–2.99(1H, m, H-9), 2.30–2.40(1H, m), 1.19–2.11(10H, m), 1.39(3H, s, H-14), 1.01(1H, d, J=5.77 Hz, H-16), 0.43(1H, d, J=7.64Hz, H-15); δ$_c$ 134.85, 127.00, 126.37, 120.02, 109.19, 90.86, 68.63, 55.19, 51.30, 43.39, 37.53, 36.72, 34.21, 29.87, 25.68, 24.97, 24.75, 19.83, 13.45; m/z(CI, CH$_4$) 375(M$^+$+1, 12%), 374(M$^+$, 16), 342(100), 329(48), 311(14), 284(28), 182(56), 148(76), 137(60), 121(48): Anal. Calcd. for C$_{22}$H$_{30}$O$_5$: C, 70.56; H, 8.07; found: C, 70.78; H, 8.28. |
| 43 | 2,4-(OCH$_3$)$_2$phenyl (10β-isomer) | — | — | White snow-like crystal. M.p. 62° C.; [α]$_D^{20.5}$ −64.21°(c. 0.0114 in CHCl$_3$); (Found C, 68.55; H, 8.14 C$_{23}$H$_{22}$O$_6$ requires C, 68.29; H, 7.97%); ν$_{max}$(Nujol): 2920, 1614, 1590, 1506, 1464, 1376, 1286, 1258, 1208, 1156, 1120, 1040, 1010, 946, 880, 832, 780, 726 cm$^{-1}$; $^1$H nmr (300MHz, CDCl$_3$) δ$_H$ 7.33(1H, d, J 8.40Hz, H-6′), 6.47 (1H, dd, J 8.40, 2.40Hz, H-5′), 6.42(1H, |

TABLE I-continued

| Ex. No. | Y | $R^1$ | $R^2$ | Physical data |
|---|---|---|---|---|
|  |  |  |  | d, J 2.40Hz, H-3'), 5.84(1H, d, J 6.60 Hz, H-10), 5.54(1H, s, H-12), 3.80, 3.79 (6H, 2×s, 2×OMe), 2.84(1H, m, H-9), 2.32 (1H, m, H-8), 1.20–2.10(10H, m, H-2a, H-2b, H-3a, H-3b, H-4, H-5, H-6a, H-6b, H-7a, H-7b), 1.37(3H, s, 1-$CH_3$), 1.00(3H, d, J 5.70Hz, 9-$CH_3$), 0.40(3H, d, J 7.50 Hz, 5-$CH_3$) ppm; m/z(CI, $CH_4$) 405([M+1]$^+$, 15), 359([-3$CH_3$]$^-$, 100), 317(6), 275 (28), 221(8), 154(22). Anal. Calc. for $C_{23}H_{32}O_6$: C, 68.29; H, 7.97%; found C, 68.55; H, 8.14; C, 68.47; H, 8.37. |
| 44 | 2,4,6-($OCH_3$)$_3$ phenyl (10β-isomer) | — | — | Colourless oil. $[\alpha]_D^{33}$ +10.6°(c 0.016/ $CHCl_3$); $\nu_{max}$(film) 2938, 1608, 1456, 1204, 1154, 1126, 1006, 954; $\delta_H$: 6.16(1H, d, J=8.09Hz, H-10), 6.13(2H, s, Ar—H), 5.52 (1H, s, H-12), 3.81(3H, s, OMe), 3.78 (2×3H, s, OMe), 2.64–2.72(1H, m), 2.29–2.38(1H, m), 1.97–2.08(2H, m), 1.68–1.84 (4H, m), 1.20–1.57(3H, m), 1.40(3H, s, H-14), 0.84–1.11(1H, m), 1.00(3H, d, J=5.73Hz, H-15), 0.72(3H, d, J=7.70Hz, H-16); m/z(CI, $CH_4$) 435(M$^+$+1, 10), 417 (8), 389(100), 371(6), 347(10), 329 (16), 221(8): Anal. Calcd. for $C_{24}H_{34}O_7$; C, 66.34; H, 7.89; found: C 66.57; H, 8.04. |
| 45 | 2,4,6-($CH_3$)$_2$ phenyl (10β-isomer) | — | — | Colourless oil. $[\alpha]_D^{22}$ +13.7 (c 0.019/ $CHCl_3$); $\nu_{max}$(film) 2938, 2874, 1452, 1376, 1208, 1106, 1076, 1008, 958, 942, 896, 880, 848, 780, 756, 724; $\delta_H$: 6.81(2H, s, Ar—H), 6.05(1H, d, J=7.57Hz, H-10), 5.55 (1H, s, H-12), 2.74–2.85(1H, m), 2.48 (3H, s, Me), 2.26–2.40(1H, m), 2.32(3H, s, Me), 2.27(3H, s, Me), 2.05–2.11(2H, m), 1.64–1.90(4H, m), 1.29–1.50(3H, m), 1.41(3H, s, H-14), 0.84–1.04(1H, m), 1.03(3H, d, J=5.91Hz, H-15), 0.64(3H, d, J=7.84Hz, H-16); $\delta_c$ : 137.22, 135.56, 135.21, 133.52, 130.81, 128.37, 102.30, 90.71, 80.94, 71.82, 51.32, 43.92, 37.59, 36.79, 34.24, 30.44, 25.72, 25.04, 24.46, 22.28, 20.70, 20.63, 19.87, 13.22; m/z (CI, $CH_4$) 387(M$^+$+1, 6), 386(8), 385(10), 341(100), 327(8), 299(8), 267(14), 221 (10), 209(4), 163(8), 133(8); Anal. Calcd. $C_{24}H_{34}O_4$: C, 74.58; H, 8.87; found: C, 74.49; H, 8.86. |
| 46 | 2,4,5-($CH_3$)$_2$ phenyl (10β-isomer) | — | — | Colourless Oil. M.P. 141° C.; $[\alpha]_D^{20}$: 55.6° (c 0.068/$CHCl_3$); $\nu_{max}$(film) 2922, 2874, 1502, 1452, 1374, 1278, 1220, 1202, 1180, 1120, 1100, 1056, 1040, 1000, 978, 954, 934, 896, 880, 820, 754; $\delta_H$: 7.32(1H, s, Ar—H), 6.99(1H, s, Ar—H), 5.94(1H, d, J=6.71Hz, H-10), 5.67(1H, s, H-12), 2.80–2.90(1H, m), 2.38–2.48(1H, m), 2.33 (2×3H, s, Me), 2.31(3H, s, Me), 2.10–2.19 (2H, m), 1.78–2.00(3H, m), 1.40–1.55(4H, m), 1.47(3H, s, H-14), 0.97–1.11(1H, m), 1.11(3H, d, J=5.75Hz, H-15), 0.55(3H, d, J=7.68Hz, H-16); $\delta_c$: 136.62, 134.02, 133.13, 131.04, 130.76, 127.09, 102.11, 91.04, 81.07, 70.00, 51.33, 43.49, 37.57, 36.73, 34.23, 29.89, 25.57, 25.01, 24.83, 19.89, 19.17, 18.73, 13.65; m/z(CI, $CH_4$) 387(M$^+$+1, 10), 386(M$^+$, 44), 354(60), 341 (84), 296(6), 282(18), 109(20), 182 (28), 160(100), 149(56), 133(38), 121 (30); Anal. Calcd. for $C_{24}H_{34}O_4$: C, 74.58; H, 8.87; found: C, 74.63; H, 8.73. |
| 47 | 4-COOH phenyl (10β-isomer) | — | — | White solid. $[\alpha]_D^{20}$ -63.2°(c 0.019/ $CHCl_3$); $\nu_{max}$(film) 2954, 2878, 2670, 2546, 2252, 1688, 1612, 1578, 1512, 1452, 1424, 1376, 1314, 1286, 1222, 1208, 1178, 1116, 1074, 1056, 1040, 1012, 980, 968, 954, 944, 908, 882, 854, 824, 802, 766, 732; $\delta_H$ 8.09(2H, d, J=8.34Hz, Ar—H), 7.45(2H, d, J=8.34Hz, Ar—H), 5.82(1H, d, J=6.63 |

TABLE I-continued

| Ex. No. | Y | R¹ | R² | Physical data |
|---|---|---|---|---|
| | | | | Hz, H-10), 5.60(1H, s, H-12), 2.76–2.83 (1H, m), 2.31–2.40(1H, m), 1.23–2.10(9H, m), 1.41(3H, s, H-14), 0.87–1.02(1H, m) 1.01(3H, d, J=5.49Hz, H-15), 0.51(3H, d, J=7.62Hz, H-16); $\delta_c$ 171.66, 147.41, 129.71, 127.33, 126.15, 102.29, 90.80, 81.07, 72.74, 51.35, 43.29, 37.42, 36.53, 34.04, 31.94, 29.05, 25.60, 24.67, 19.78, 13.42; m/z(CI, CH$_4$) 389(M$^+$+1.8), 329 (100), 283(36), 267(20), 219(26), 177 (80), 129(64). Anal. Calc. for C$_{22}$H$_{20}$O$_6$: C, 68.02; H, 7.27; found: C, 67.77; H, 7.31. |
| 48 | 4-Phenyl-piperazino (10α-isomer) | — | — | White solid. M.p. 149–150° C.; $[\alpha]_D^{20}$ + 16.7°(c 1.24 in CHCl$_3$); $\nu_{max}$(film): 2924, 1600, 1504, 1450, 1378, 1238, 1206, 1158, 1042, 984, 926, 880, 750, 690 cm$^{-1}$; $^1$H NMR (300MHz, CDCl$_3$) $\delta_H$ 7.34(2H, m), 7.03 (2H, d, J=8.0Hz, H-2", H-5"), 6.92(1H, t, J=7.3Hz, H-4"), 5.39(1H, s, H-12), 4.18(1H, d, J=10.2Hz), 3.29–3.21(6H, m), 2.90(2H, m), 2.70(1H, m), 2.45(1H, m), 2.13(1H, m), 1.95(1H, m), 1.75(2H, m), 1.70–1.20(8H, m), 1.20–1.00(4H, m), .93(3H, d, J=7.1Hz, 6-methyl) ppm; $^{13}$C NMR (76MHz, CDCl$_3$) $\delta_c$ 151.6, 128.9, 119.3, 116.0, 103.8, 91.6, 90.4, 80.3, 51.7, 49.5, 47.2, 45.8, 37.4, 36.3, 34.3, 28.5, 25.9, 24.8, 21.6, 20.3, 13.4 ppm; MS (CI, CH$_4$) m/e 429(M$^+$+1, 88). Anal. Calcd. for C$_{25}$H$_{36}$N$_2$O$_4$: C, 70.06, H, 8.47, N, 6.53; Found: C, 69.74, H, 8.38, N, 6.35. |
| 49 | 4-(2'-methoxyphenyl)-piperazino (10α-isomer) | — | — | White solid. M.p. 158–159° C.; $[\alpha]_D^{20}$ + 12.2°(c. 0.752 in CHCl$_3$); $\nu_{max}$(film): 2936, 1594, 1500, 1448, 1376, 1240, 1180, 1118, 1058, 982, 926, 880, 828, 750 cm$^{-1}$; $^1$H NMR (300MHz, CDCl$_3$) $\delta_H$ 7.10–6.80(4H, m, Ar—H), 5.30(1H, s, H-12), 4.07(1H, d, J=10.2Hz, H-10), 3.85(3H, s, —OMe), 3.30–2.95(6H, m), 2.95–2.75(2H, m), 2.61 (1H, m), 2.35(1H, m), 2.00(1H, m), 1.85 (1H, m), 1.70(2H, m), 1.60–1.15(9H, m), 1.15–0.90(4H, m), 0.84(3H, 7.2Hz, 6-methyl) ppm; $^{13}$C NMR (76MHz, CDCl$_3$) $\delta_c$ 152.3, 141.8, 122.5, 120.9, 118.1, 111.2, 103.8, 91.6, 90.4, 80.4, 55.3, 51.8, 51.1, 45.9, 37.4, 36.4, 34.3, 28.5, 26.0, 24.8, 21.7, 21.7, 20.3, 13.4 ppm; MS (CI, CH$_4$) m/e 459(M$^+$+1, 55). Anal. Calcd. for C$_{26}$H$_{34}$N$_3$O$_5$: C, 68.10, H, 8.35, N, 6.11; Found: C, 67.74, H, 8.35, N, 5.83. |
| 50 | 4-(4'-fluorophenyl)-piperazino (10α-isomer) | — | — | White solid. M.p. 157–158° C.; $[\alpha]_D^{20}$ + 23.1°(c 0.743 in CHCl$_3$); $\nu_{max}$(film): 2933, 2842, 1704, 1689, 1654, 1617, 1560, 1516, 1456, 1381, 1314, 1249, 1227, 1205, 1160, 1135, 1111, 1061, 1047, 1027, 985, 921, 803, 853, 822, 697 cm$^{-1}$; $^1$H NMR (300 MHz, CDCl$_3$) $\delta_H$ 7.00–6.80(4H, m Ar—H), 5.29(1H, s, H-12), 4.07(1H, d, J=10.2 Hz), 3.15–3.05(6H, m), 2.83(2H, m), 2.60 (1H, m), 2.35(1H, m), 2.00(1H, m), 1.90 (1H, m), 1.73(2H, m), 1.70–1.10(9H, m), 1.10–0.90(4H, m), 0.83(3H, d, J=7.1 Hz, 6-methyl) ppm; $^{13}$C NMR (76MHz, CDCl$_3$) $\delta_c$ 156.8 (d, $^1J_{C-F}$=238Hz), 148.2(d, $^4J_{C-F}$= 1.96Hz), 117.6(d, $^3J_{C-F}$=7.55Hz), 115.2(d, $^2J_{C-F}$=21.9Hz), 103.7, 91.5, 90.3, 80.2, 51.6, 50.4, 47.1, 45.7, 37.3, 36.2, 34.2, 28.4, 25.9, 24.7, 21.5, 20.2, 13.3 ppm; MS (CI, CH$_4$) m/e 447(M$^+$+1, +82). Anal. Calcd. for C$_{25}$H$_{35}$N$_3$O$_4$F: C, 67.24, H, 7.90, N, 6.27; Found: C, 67.28, H, 8.01, N, 5.95. |
| 51 | 4-(2'-pyridyl)-piperazino (10α-isomer) | — | — | White solid. M.p. 146–147° C.; $[\alpha]_D^{20}$ +16.4° c 1.34 in CHCl$_3$); $\nu_{max}$(film) 2926, 2872, 1596, 1564, 1482, 1346, 1378, 1312, 1248, 1208, 1160, 1132, 1056, 1026, 980, 926, |

TABLE I-continued

| Ex. No. | Y | R¹ | R² | Physical data |
|---|---|---|---|---|
| | | | | 880, 850, 828, 744, 732 cm⁻¹; ¹H NMR (300 MHz, CDCl₃) δ$_H$ 8.17(1H, dd, J=1.3, 5.0 Hz, H-6"), 7.44(1H, td, J=1.8, 3.4Hz, H-4"), 6.64–6.55(2H, m, H-3" & H-5"), 5.27(1H, s, H-12), 4.07(1H, d, J=10.3 Hz, H-10), 3.52–3.48(4H, m, H-3' & H-5'), 3.10–3.05(2H, m), 2.79–2.74(2H, m), 2.76(1H, m), 2.32(1H, m), 2.02–1.80 (2H, m), 1.70–1.65(2H, m), 1.50–1.20 (8H, m), 1.10–0.90(4H, m), 0.83(3H, d, J=7.2Hz, 6-methyl) ppm; ¹³C NMR (76 MHz, CDCl₃) δ$_c$ 153.6, 147.8, 137.2, 112.8, 107.0, 103.8, 91.6, 90.6, 80.3, 51.7, 47.1, 45.8, 45.5, 37.3, 36.3, 34.3, 28.5, 25.9, 24.7, 21.6, 20.3, 13.4 ppm; MS (CI, NH₃) m/e 430(M⁺+1, 100); Anal. Calcd. for C₂₄H₃₅N₃O₄: C, 67.11, H, 8.21, N, 9.78; Found: C, 67.01, H, 8.22, N, 9.55. |
| 52 | 4-(3'-trifluoromethyl-phenyl)-piperazino (10α-isomer) | | | White solid. M.p. 126–127° C.; [α]$_D^{20}$ + 23.0°(c. 0.543 in CHCl₃); ν$_{max}$(film): 2928, 2874, 1612, 1588, 1496, 1450, 1412, 1378, 1356, 1320, 1266, 1242, 1208, 1164, 1122, 1100, 1054, 986, 948, 926, 880, 860, 828, 788, 732, 696, 648 cm⁻¹; ¹H NMR (300MHz, CDCl₃) δ$_H$ 7.33(1H, m, H-5"), 7.10–7.02(3H, m, Ar—H), 5.30(1H, s, H-12), 4.09(1H, d, J=10.2Hz, H-10), 3.40–3.05(6H, m), 2.84(2H, m), 2.65 (1H, m), 2.35(1H, m), 2.00(1H, m), 1.85 (1H, m), 1.80–1.60(2H, m), 1.60–1.15 (10H, m), 1.15–0.90(4H, m), 0.84(3H, d, J=7.1Hz) ppm; ¹³C NMR (76MHz, CDCl₃) δ$_c$ 151.7, 129.4, 118.7, 115.4, 111.9, 103.9, 91.6, 90.5, 80.3, 51.7, 49.0, 47.0, 45.8, 37.4, 36.3, 34.3, 28.5, 25.9, 24.8, 21.6, 20.3, 13.4 ppm; ¹⁹F NMR (282 MHz, CDCl₃) δ$_F$ 63.9 ppm; MS (CI, CH₄) m/e 497(M⁺+1, 58). Anal. Calcd. for C₂₆H₃₅N₃O₄F₃: C, 62.89, H, 7.10, N, 5.64; Found: C, 62.82, H, 7.27, N, 5.58. |
| 53 | 4-Fluorophenyl (10β-isomer) | — | — | White solid. M.P. 133.6–134.8° C.; [α]$_D^{20}$ − 35.66°(c 0.83, CHCl₃); δ$_F$: −118.00; IR (neat) ν$_{max}$: 2952, 2873, 1604, 1510, 1452, 1376, 1222, 1110, 1040, 1010, 944, 906, 882, 838, 782; δ$_H$: 7.29–7.24(2H, m, Ph), 7.04–6.97(2H, m, Ph), 5.70(1H, d, H-10, J=6.70Hz), 5.55(1H, s, H-12), 2.77–2.65(1H, m), 2.39–2.28(1H, m), 2.10–1.97(2H, m), 1.90–1.82(1H, m), 1.78–1.64(2H, m), 1.49–1.17(8H, m), 0.99(3H, d, 6-Me, J=5.75Hz), 0.48(3H, d, 9-Me, J=7.68Hz); δ$_c$: 162.10(d, Ph, J$_{CF}$=244.0Hz), 137.42(d, Ph, J$_{CF}$=3.09 Hz), 128.30(d, Ph, J$_{CF}$=7.84Hz), 115.16 (d, Ph, J$_{CF}$=21.27Hz), 102.92, 91.55, 81.75, 73.15, 52.09, 44.05, 38.14, 37.30, 34.82, 32.78, 26.35, 25.57, 25.42, 20.52, 14.29; MS (CI positive, NH₃) m/z: 382 (MNH₄⁺, 2×¹³C, 4%), 381(MNH₄⁺, ¹³C, 25%), 380(MNH₄⁺, base peak), 363(MH⁺, 6%); Anal Calcd. for C₂₁H₂₇O₄F C 69.59, H 7.51; found C 69.51, H 7.62. |
| 54 | 1-(2-pyrimidyl)-piperazino (10β-isomer) | — | — | White solid. M.p. 147.1–147.5° C.; [α]$_D^{20}$: +14.3°(c=0.86, CHCl₃); IR (KBr) ν$_{max}$ 2988, 2970, 2948, 2918, 2870, 2854, 1588, 1546, 1502, 1452, 1438, 1430, 1396, 1376, 1308, 1268, 1186, 1160, 1132, 1114, 1102, 1060, 1044, 1022, 980, 940, 926, 880, 852, 826, 798, 742, 694, 640; δ$_H$: 8.27 (2H, d, o-Ph, J=4.8Hz), 6.43(1H, t, p-Ph, J=4.8Hz), 5.27(1H, s, H-12), 4.05 (1H, d, H-10, J=10.2Hz), 3.87–3.72(4H, m, 2×NCH₃), 3.08–3.01(2H, m), 2.75–2.59 (4H, 2×NCH₃), 2.38–2.27(1H, m), 2.02–1.37(8H, m), 1.34(3H, s, 3-Me), 1.33–1.17(1H, m), 0.94(3H, d, 6-Me, J=6.1 |

TABLE I-continued

| Ex. No. | Y | R¹ | R² | Physical data |
|---|---|---|---|---|
| | | | | Hz), 0.85(3H, d, 9-Me, J=7.16Hz); $\delta_c$: 162.39, 158.31, 110.17, 104.56, 92.34, 91.49, 80.99, 52.44, 47.95, 46.56, 44.76, 38.07, 37.02, 34.99, 29.20, 26.66, 25.44, 22.34, 20.97, 14.22; MS (CI, CH$_4$) m/z: 432(MH$^+$, $^{13}$C, 5%), 431(MH$^+$, 33%); Anal. calcd for C$_{22}$H$_{34}$N$_4$O$_4$: C 64.16, H 7.96, N 13.01; found C 64.09, H 8.07, N 12.86. |
| 55 | 1-(4-Chlorophenyl)-piperazino 10α-isomer | — | — | White solid. M.p. 140.7–142.8° C.; $[\alpha]_D^{20}$: +9.41°(c=1.01, CHCl$_3$); IR (KBr) $v_{max}$: 2976, 2952, 2934, 2894, 2872, 2842, 1596, 1502, 1454, 1378, 1350, 1316, 1286, 1248, 1206, 1184, 1160, 1136, 1108, 1060, 1046, 1026, 956, 982, 882, 852, 816, 698, 666, 518; $\delta_H$: 7.20(2H, d, Ph, J=9.0Hz), 6.85(2H, d, Ph, J=9.02Hz), 5.30(1H, s, H-12), 4.09(1H, d, H-10, J=10.23Hz), 3.20–3.07(8H, m, 4×NCH$_2$), 2.86–1.20 (15H, m), 0.96(3H, d, 6-Me, J=6.09Hz), 0.84(3H, d, 9-Me, J=7.18Hz); $\delta_c$: 150.93, 129.49, 124.75, 117.83, 104.57, 92.29, 91.11, 81.02, 52.39, 50.18, 47.74, 46.51, 38.08, 36.99, 34.97, 29.21, 26.65, 25.45, 22.33, 20.97, 14.14; MS (CI positive, CH$_4$) m/z: 465(MH$^+$, $^{37}$Cl, 2%), 464(MH$^+$, $^{13}$C, 0.4%), 463(MH$^+$, 6%); Anal. Calcd for C$_{25}$H$_{15}$N$_2$O$_4$Cl: C 64.85, H 7.62, N 6.05; found: C 64.68, H 7.66, N 5.89. |
| 56 | 1-(3-Chlorophenyl-piperazino 10α-isomer | — | — | White solid. M.p. 137.3–137.8° C.; $[\alpha]_D^{20}$: +12.13°(c=0.89, CHCl$_3$); IR (KBr) $v_{max}$ 2976, 2948, 2922, 2876, 2864, 2848, 2826, 1598, 1566, 1486, 1452, 1430, 1412, 1378, 1360, 1328, 1312, 1284, 1274, 1264, 1244, 1206, 1184, 1158, 1136, 1116, 1102, 1086, 1042, 1028, 988, 942, 928, 880, 854, 832, 782, 774, 680: $\delta_H$: 7.18–7.12(1H, m, Ph), 6.88–6.77(3H, m, Ph), 5.30(1H, s, H-12), 4.08(1H, d, H-10, J=10.21Hz), 3.24–3.12(6H, m, 3×NCH$_2$), 2.84–2.78 (2H, m, NCH$_2$), 2.66–2.59(1H, m), 2.41–2.30(1H, m), 2.05–1.20(13H, m), 0.96 (3H, d, 6-Me, J=6.06Hz), 0.84(3H, d, 9-Me, J=7.17Hz); $\delta_c$: 153.36, 135.54, 130.59, 119.58, 116.33, 114.58, 104.63, 92.34, 91.18, 81.05, 52.44, 49.75, 47.76, 46.55, 38.11, 37.02, 35.00, 29.25, 26.67, 25.48, 22.37, 20.99, 14.16; MS (ES) m/z: 465(MH$^+$, $^{13}$C, 10%), 464(MH$^+$, $^{13}$C, 9%), 463(MH$^+$, 100%); Anal. Calcd for C$_{25}$H$_{35}$N$_2$O$_4$Cl: C 64.85, H 7.62, N 6.05, found: C 64.91, 7.73, N 6.00. |
| 57 | 1-(2-Chlorophenyl)-piperazino | — | — | White solid. M.p. 72–75° C., $[\alpha]_D^{20}$ −5.15° (c 1.01, CHCl$_3$): IR (neat) $v_{max}$3062, 2926, 2870, 2360, 1588, 1480, 1450, 1376, 1232, 1206, 1124, 1040, 984, 926, 880, 828, 762, 668; $\delta_H$: 7.37–6.92(4H, m, Ph), 5.32(1H, s, H-12), 4.09(1H, d, H-10, J=10.21Hz), 3.23–3.05(8H, m, 4×NCH$_2$), 2.67–2.60(1H, m, .H-9), 2.41(1H, m), 2.37–1.20(13H, m), 0.96(3H, d, 6-Me, J=6.14Hz), 0.85(3H, d, 9-Me, J=7.19 Hz); $\delta_c$: 150.37, 131.31, 129.50, 128.11, 124.00, 120.99, 104.62, 92.40, 91.29, 81.07, 52.49, 52.38, 46.61, 38.09, 37.07, 35.02, 29.26, 26.72, 25.47, 22.39, 21.00, 14.21; MS (ES positive) m/z: 465(MH$^+$, $^{39}$Cl, 20%), 464(MH$^+$, $^{13}$C, 19%), 463(MH$^+$, 100%); Anal. Calcd for C$_{28}$H$_{38}$N$_2$O$_4$Cl: C 64.05, H 7.62, N 6.05; found: C 64.92, H 7.67, N 5.77. |
| 58 | 1-(4-Methoxyphenyl)-piperazino | — | — | White solid. M.p. 147.6–148.4° C.; $[\alpha]_D^{20}$: +9.07°(c 1.08, CHCl$_3$): IR (KBr) $v_{max}$2958, 2924, 2846, 2810, 1512, 1464, 1448, 1420, 1378, 1350, 1326, 1310, 1292, 1264, 1248, 1206, 1182, 1160, 1134, 1108, 1086, 1060, 1038, 1026, 1010, 984, 942, 926, 880, 852, 824, 814, 800; $\delta_H$: 6.93–6.81(4H, |

TABLE I-continued

| Ex. No. | Y | R¹ | R² | Physical data |
|---|---|---|---|---|
| | | | | m, Ph), 5.30(1H, s, H-12), 4.08(1H, d, H-10, J=10.20Hz), 3.77(3H, s, OMe), 3.20–3.04(6H, m, 3×NCH₃), 2.86–2.80 (2H, m, NCH₃), 2.66–2.59(1H, m), 2.41– 2.31(1H, m), 2.05–1.21(13H, m), 0.96 (3H, d, 6-Me, J=6.08Hz), 0.84(3H, d, 9-Me, J=7.16Hz); $\delta_c$: 154.22, 146.81, 118.81, 115.00, 104.53, 92.27, 91.08, 81.03, 56.22, 52.40, 51.70, 47.93, 46.54, 38.07, 37.00, 34.98, 29.22, 26.64, 25.46, 22.34, 20.98, 14.12; MS (ES positive) m/z: 459(MH⁺, 100%), 458(M⁺, 58%) Anal. Calcd for C₂₆H₃₈N₂O₄: C 68.10, H 8.35, N 6.11; found: C 68.16, H 8.42, N 5.97. |
| 59 | 1-(ortho-Tolyl)-piperazino 10α-isomer | — | — | White solid. m.p. 141.6–142.8° C.; $[\alpha]_D^{20}$ +12.55°(c 1.02, CHCl₃); IR (neat) vhd max 3026, 3021, 2926, 2872, 2360, 1598, 1492, 1448, 1376, 1328, 1306, 1258, 1226, 1206, 1180, 1156, 1132, 1118, 1056, 1040, 1026, 982, 958, 926, 880, 850, 828, 762, 722, 668; $\delta_H$: 7.19–7.14(2H, m, Ph), 7.07–6.94 (2H, m, Ph), 5.33(1H, s, H-12), 4.10 (1H, d, H-10, J=10.17Hz), 3.19–3.14(2H, m, NCH₂), 2.97–2.79(6H, m, 3×NCH₂), 2.71–2.59(1H, m, H-9), 2.37(1H, m), 2.32(3H, s, PhMe), 2.07–2.00(1H, m), 1.71–1.17(11H, m), 0.97(3H, d, 6-Me, J=6.1Hz), 0.87(3H, d, 9-Me, J=7.2Hz); $\delta_c$: 174.96, 152.60, 133.43, 131.66, 127.07, 123.47, 139.54, 104.61, 92.45, 91.36, 81.08, 52.84, 52.48, 46.59, 38.07, 37.05, 35.00, 29.25, 26.75, 25.55, 22.38, 20.99, 18.64, 14.22; MS (CI CH₄) m/z: 444 (MH⁺, ¹³C, 5.1%), 443(MH⁺, 18%), 442(M⁺, 7.6%); Anal. Calcd for C₂₆H₃₈N₂O₄: C 70.56, H 8.65, N 6.33; found C 70.43, H 8.54, N 6.28. |
| 60 | 4-Benzylpiperidino 10α-isomer | — | — | White solid. M.p. 137.6–138.9° C.; $[\alpha]_D^{20}$: +10.82°(c 0.98, CHCl₃): IR (neat) $v_{max}$: 2924, 2870, 1452, 1376, 1206, 1132, 1098, 1056, 970, 926, 880, 828, 746, 700; $\delta_H$: 7.28–7.24(2H, m, Ph), 7.19–7.12(3H, m, Ph), 5.25(1H, s, H-12), 4.00(1H, d, H-10, J=10.16Hz), 3.00–2.86(2H, m), 2.69– 2.27(6H, m), 2.02–1.41(10H, m), 1.38 (3H, s, 3-Me), 1.33–1.12(4H, m), 1.09– 0.97(1H, m), 0.93(3H, d, 6-Me, J=6.12 Hz), 0.78(3H, d, 9-Me, J=7.18Hz); $\delta_c$: 141.60(Ph), 129.75(Ph), 128.73(Ph), 126.28(Ph), 104.44, 92.40, 91.75, 81.06, 52.46, 46.64, 44.16, 44.03, 38.85, 38.02, 37.02, 34.99, 33.49, 33.18, 29.36, 26.72, 25.41, 22.32, 20.97, 14.20; MS (CI positive, NH₃) m/z: 444(MH⁺, 2×¹³C, 2%), 443(MH⁺, ¹³C, 12%), 442(MH⁺, 38%), 441(M⁺, 1%); Anal Calcd. For C₂₇H₃₉NO₄: C 73.44, H 8.90, N 3.17; found C 73.25, H 8.85, N 3.14. |
| 61 | 6-Methoxynaphthyl 10α- and 10β-isomers | — | — | $\delta_H$: 7.73–7.70(3H, m, Ph), 7.59–7.55(1H, m, Ph), 7.13–7.10(2H, m, Ph), 4.50(1H, d, H-10, J=10.64Hz), 3.91(3H, s, OMe), 2.72–2.65(1H, m), 2.49–2.43(1H, m), 2.10–2.02(1H, m), 1.96–1.87(1H, m), 1.81–1.74(1H, m), 1.68–1.53(4H, m), 1.46 (3H, s, 3-Me), 1.42–1.24(3H, m), 1.13– 1.05(1H, m), 0.99(3H, d, 6-Me, J=6.15 Hz), 0.55(3H, d, 9-Me, J=7.19Hz); $\delta_c$: 158.18, 136.70, 135.07, 130.13, 129.28, 127.65, 127.01, 126.46, 119.24, 106.32, 104.92, 92.76, 81.36, 79.15, 55.93, 52.70, 46.78, 38.12, 37.05, 34.93, 34.55, 26.75, 25.51, 22.20, 21.01, 14.80; MS (ES positive) m/z: 424(MH⁺, 4%), $\delta_H$: 7.74– 7.67(3H, m, Ph), 7.39–7.35(1H, m, Ph), 7.14–7.11(2H, m, Ph), 5.86(1H, d, H-10, J=3.72Hz), 5.54(1H, s, H-12), 3.91(3H, s, OMe), 2.86–2.78(1H, m), 2.40–2.30 (1H, m), 2.09–1.58(5H, m), 1.51–1.23 |

TABLE I-continued

| Ex. No. | Y | R¹ | R² | Physical data |
|---------|---|----|----|---------------|
|         |   |    |    | (7H, m), 0.99(3H, d, 6-Me, J=5.58Hz), 0.94–0.88(1H, m), 0.52(3H, d, 9-Me, J=7.65Hz); $\delta_c$: 157.97, 137.12, 134.08, 130.11, 129.39, 126.83, 126.19, 124.98, 119.23, 106.29, 103.09, 91.72, 81.99, 73.86, 55.04, 52.29, 44.28, 38.29, 37.45, 34.97, 32.96, 26.51, 25.70, 25.57, 20.67, 14.52; MS (CI positive, $CH_4$) m/z: 426($MH^+$, $^{13}C$, 2%), 425($MH^+$, 8%), 424($M^+$, 7%). |

EXAMPLE 62

The parasiticidal activity of compounds of the invention was investigated by means of the following tests.

Abbreviations used in the examples:
$CO_2$=carbon dioxide
DMSO=dimethylsulphoxide
ED=dermal cell line of a horse
EDTA=ethylenediaminetetraacetic acid
FCS=fetal calf serum
RPMI=growth medium for cell cultures
rpm=revolutions per minute
VERO=kidney cell line of the African green monkey

(a) Screening of Compounds Against *Neospora Caninum* Cell Cultures In Vitro Screening was conducted in 96-well plates (Falcon 3872). A monolayer of host cells (VERO or ED) were placed on a cell culture plate. Non-infected mono-layers of cells were cultured in two 50 ml tissue culture bottles (50 cm³ cell culture area). The cell layer was detached with trypsin-EDTA (5 ml. Gibco 45300-019) in a $CO_2$-culture cupboard at 37° C. After 10 minutes, most of the cells were detached. The cells were transferred with a 5 ml pipette into a 50 ml centrifuge tube (Greiner, B769331) containing about 1 ml warmed fetal calf serum. After centrifugation for 5 minutes at 1500 rpm (Varifuge 3.0, Heraeus), the liquid was removed and the cell pellet suspended in RPMI medium (100 ml, 95% RPMI 1640, 2% FCS, 1% L-glutamine, 1% sodium hydrogen carbonate, 1% penicillin/streptomycin). The cell suspension was pipetted into six 96-well plates at 150 µl per well. The coated cell culture plates were placed in an incubation cupboard at 37° C. under 5% $CO_2$ for 24 hours. The cells were then infected with *Neospora caninum* tachyzoites at a concentration of 48,000 tachyzoites per well. This was followed by incubation at 37° C. under 5% $CO_2$ for 24 hours.

The test compounds (0.5–1.5 mg) were weighed into 1.5 ml eppendorf vessels and dissolved in 1 ml dimethyl sulphoxide, corresponding to a dilution of about $1\times10^{-3}$ g $ml^{-1}$. The medium used for further dilution consisted of 87% RPMI 1640, 10% FCS, 1% L-glutamine, 1% sodium hydrogen carbonate, 1% penicillin/streptomycin. In the first screening, concentrations of $10^{-5}$, $10^{-5}$ and $10^{-7}$ g $ml^{-1}$ were used. The diluted preparations were then transferred to the cell culture plates at a volume of 150 µl per well after 24 hour infection with *Neospora caninum*. For the first row, untreated medium was used; this row contained infected and uninfected cells as controls. The cell plate was incubated at 37° C. under 5% $CO_2$ for 5 days. Microscopic evaluation was conducted 4 days after treatment and 5 days after infection at a magnification of 25×10 in an inverse microscope according to the following evaluation scheme.

| Evaluation | Observable effect |
|------------|-------------------|
| 0 = no effect | monolayer completely destroyed |
| 1 = weak effect | monolayer partly destroyed, parasite clumps can be seen |
| 2 = full effect | monolayer intact, no tachyzoites observable |
| T = cytotoxic | cells are dead, lysed |

The results are set out in Table II below:—

TABLE II

| Example No. | Dose (g/ml) | | | |
|---|---|---|---|---|
|   | $10^{-5}$ | $10^{-6}$ | $10^{-7}$ | $10^{-8}$ |
| 2  | 1   | 1 | 0 | — |
| 15 | T/1 | 1 | 1 | 0 |
| 18 | 2   | 1 | 0 | — |
| 19 | T   | 0 | — | — |
| 20 | T/1 | 1 | 1 | 0 |
| 21 | 2   | 0 | — | — |
| 23 | T/2 | 0 | — | — |
| 24 | 1   | 0 | — | — |
| 25 | T/1 | 1 | 1 | 0 |
| 30 | 1   | 0 | — | — |
| 31 | 2   | 1 | 0 | — |
| 32 | 2   | 0 | — | — |
| Artemisinin | 0 | — | — | — |

(b) Screening of Compounds Again *Eimeria Tenella* Cell Cultures In Vitro

Cells from kidneys of 19 day old chicks are cultured as monolayers in 96-well plates (Falcon 3872) in a medium of Hanks lactalbumine hydrolysate, 5% fetal calf serum, 1% glutamine and 1% non-essential amino acids. After two days at 42° C. under 5% $CO_2$, the culture was infected with excised sporozoites of *Eimeria tenella* at about 30.00 per well. Test compounds were dissolved in DKSO and diluted with culture medium to a maximum end concentration of 10 µg $ml^{-1}$. The dilution steps were 1:10. On day 5 post infection, the cultures were evaluated under a microscope at 100-fold magnification and the condition of the host cells and the amount of intact schizonts and free merozoites was determined. Effectiveness was rated as follows:

| Evaluation | Observable effect |
|------------|-------------------|
| 3 = very active | no intact parasites/well |
| 2 = active | 1–6 parasites per well |

-continued

| Evaluation | Observable effect |
|---|---|
| 1 = weakly active | up to 1 intact schizont/optical field of vision |
| 0 = inactive | >1 intact schizont/optical field of vision |
| T = cytotoxic | host cells are dead |

The results are set out in Table III below:—

TABLE III

| | Dose (g/ml) | | | |
|---|---|---|---|---|
| Example No. | $10^{-5}$ | $10^{-6}$ | $10^{-7}$ | $10^{-8}$ |
| 2 | 2 | 2 | 1 | 0 |
| 15 | 2 | 2 | 1 | 0 |
| 18 | T | T | 1 | 0 |
| 19 | T | T | 1 | 0 |
| 20 | T | T/2 | 0 | — |
| 21 | T/2 | 0 | — | — |
| 23 | T | T/2 | 0 | — |
| 24 | 2 | 1 | 0 | — |
| 25 | 2 | 1 | 1 | 0 |
| 30 | T | 2 | 0 | — |
| 31 | T | 1 | 0 | — |
| 32 | T | 2 | 0 | — |
| Artemisinin | 2 | 1 | 0 | — |

(c) In Vitro Screening Against *Plasmodium Falciparum*

Two parasite strains—W2 resistant to chloroquine, and D6 sensitive to chloroquine but resistant to mefloquine were used. In Table IV below, the best compounds should show no cross resistance between the two strains.

The assay relies on incorporation of radiolabelled hypoxanthine by the parasite and inhibition of incorporation is attributed to activity of known or candidate antimalarial drugs. For each assay, proven antimalarials such as chloroquine, mefloquine, quinine, artemisinin and pyrimethamine were used as controls. The incubation period was 66 hours, and the starting parasitemia was 0.2% with 1% hematocrit. The medium was an RPMI-1640 culture with no folate or p-aminobenzoic acid. Albumax rather than 10% normal heat inactivated human plasma was used as, with Albumax, less protein binding is observed, and compounds elicit slightly higher activities in this model. If a compound was submitted with no prior knowledge of activity, it was dissolved directly in dimethyl sulphoxide (DMSO), and diluted 400 fold with complete culture medium. The unknown compound was started at a maximum concentration of 50,000 ng ml$^{-1}$ and sequentially diluted 2-fold for 11 times to give a concentration range of 1048 fold. These dilutions were performed automatically by a Biomek 1000 Liquid Handling System in 96-well microtiter plates. The diluted drugs were then transferred to test plates, 200 μl of parasitized erythrocytes were added, and incubated at 37° C. in a controlled environment of 5% $CO_2$, 5% $O_2$ and 90% $N_2$. After 42 hours, 25 μl of $^3$H-hypoxanthine was added, and the plates incubated for an additional 24 hours. After 66 hours, the plates were frozen at −70° C. to lyse the red cells, and then thawed and harvested onto glass fiber filter mats in a 96-well harvester. The filter mats were then counted in a scintillation counter. For each drug, the concentration response profile was determined and 50%, 90% and 10% inhibitory concentrations ($IC_{50}$ $IC_{90}$ and $IC_{10}$) were determined by a non-linear logistic dose response analysis program.

A prescreen format can be used wherein a 3-dilution assay may be used to determine activity at high medium or low concentrations. The concentrations were selected as 50,000, 500 and 50 ng ml$^{-1}$. These were performed in duplicate on a 96-well format plate with 14 test compounds and one known (standard) compound per plate. The system was automated with a Biomek diluter for mixing and diluting the drugs, and adding drugs and parasites to a test plate. In the prescreen format, if the ANALYSIS FIELD (AP) has a "<", then the compound was "very active" and the IC values are most likely to be below the last dilution value (in nanograms/ml), which is listed next to AF. In most cases, these compounds were run again at lower starting concentration to determine the true IC value. If the AF has a ">", then the IC value is greater than the prescreen dilution value; thus "AF>250" means that the IC value is greater than 250 ng ml$^{-1}$ and no further screening is carried out. In such cases, values of 0.00 are entered for IC values.

The results are set out in Table IV below:—

TABLE IV

| | In vitro activity:$IC_{50}$;$IC_{90}$;($IC_{10}$)ng/ml | |
|---|---|---|
| Example No. | W2 Strain (Chloroquine resistant) | D6 Strain (Chloroquine sensitive) |
| IA(10α-isomer) | 0.69; 0.97 | 0.64; 1.24 |
| IB(10β-isomer) | 0.69; 0.98 | 0.74; 1.36 |
| 2 | 0.31; 0.52; (0.19) | 0.73; 0.99; (0.53) |
| 4 | 0.84; 1.74; (0.40) | 1.05; 2.10; (0.52) |
| 12 | 0.78; 1.32; (0.47) | 0.77; 1.70; (0.35) |
| 15 | 0.66; 0.84; (0.52) | 0.61; 0.78; (0.48) |
| 16 | 0.64; 0.84; (0.49) | 0.61; 0.78; (0.48) |
| 18 | 0.23; 0.33; (0.17) | 0.28; 0.82; (0.09) |
| 19 | 0.33; 0.43; (0.25) | 0.39; 0.80; (0.19) |
| 20 | 5.81; 12.77; (2.64) | 9.40; 12.93; (6.84) |
| 21 | 0.00; 0.00 250AF < 0 | 1.77; 3.96; (0.79) |
| 23 | 0.00; 0.00; AF > 250 | 0.00; 0.00; AF > 250 |
| 24 | 0.77; 1.30; (0.46) | 1.17; 2.10; (0.65) |
| 25 | 0.11; 0.17; (0.07) | 0.09; 0.35; (0.02) |
| 26 | 0.00; 0.00 AF < 4 | 9.05; 16.24; (5.05) |
| 30 | 0.00; 0.00; 250AF < 0 | 11.20; 18.61; (6.74) |
| 31 | 0.29; 0.68; (0.12) | 1.35; 2.42; (0.75) |
| 32 | 0.45; 0.92; (0.22) | 2.45; 3.97; (1.51) |
| 36 | 0.26; 0.61; (0.11) | 0.38; 0.77; (0.19) |
| 38 | 1.23; 2.76 (0.55) | 0.90; 3.69; (0.22) |
| 41 | 0.73; 1.7; (0.30) | 1.53; 2.04; (1.16) |
| 44 | 0.3318; 0.8168; (0.13) | 0.69; 1.67; (0.29) |

What is claimed is:
1. A compound of the general formula I

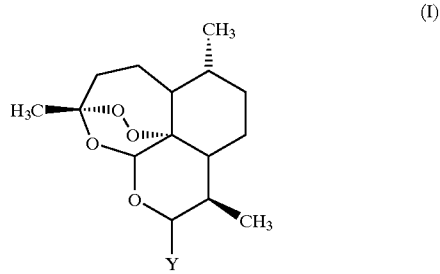

(I)

or a salt thereof,
in which
Y represents a group —NR$^1$R$^2$; where
R$^1$ and R$^2$ together with the interadjacent nitrogen atom represent an optionally substituted nonaromatic heterocyclic group.

2. A pharmaceutical composition which comprises a carrier and, as active ingredient, a compound of the general formula I according to claim 1.

3. A process for the preparation of a compound of the general formula I according to claim 1 which comprises reacting a compound of the general formula II

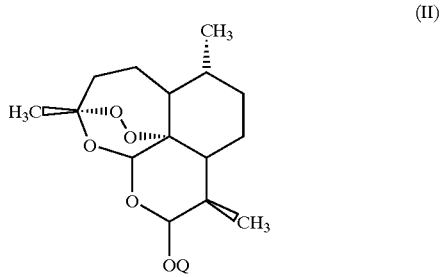

(II)

in which Q represents a hydrogen atom or trimethylsilyl group, with a suitable halogenating agent to form a compound of the general formula I in which Y represents a halogen atom, further comprising reacting the compound thus formed with an amine of the general formula $HNR^1R^2$ where $R^1$ and $R^2$ are as defined in claim 1 form a compound of general formula I in which Y represents a group —$NR^1R^2$ where $R^1$ and $R^2$ are as defined above in claim 1.

4. The compound of claim 1 wherein said optionally substituted nonaromatic heterocyclic group is piperazinyl, morpholinyl, thiomorpholinyl, or mopholinosulphonyl.

5. The compound of claim 4, wherein said optionally substituted nonaromatic heterocyclic group is mopholinosulphonyl.

6. The compound of claim 5, which is 10α-(4'-(S,S-dioxothiomorpholin-1'-yl)-10-deoxo-10-dihydroartemisinin.

7. The compound of claim 4, which is 10α-(4'-benzylpiperazin-1'-yl)-10-deoxo-10-dihydroartemisinin.

8. The compound of claim 4, which is 10α-(morpholino) 10-deoxo-10-dihydroartemisinin.

9. The compound of claim 4 which is 10α-(1-(2-pyrimidyl)-piperazino)-10-deoxo-10-dihydroartemisinin.

* * * * *